US012286880B2

(12) United States Patent
Kadayam Viswanathan et al.

(10) Patent No.: US 12,286,880 B2
(45) Date of Patent: Apr. 29, 2025

(54) METHODS AND SYSTEMS FOR CHARACTERIZING PROPERTIES OF RESERVOIR ROCK

(71) Applicant: SCHLUMBERGER TECHNOLOGY CORPORATION, Sugar Land, TX (US)

(72) Inventors: Ravinath Kausik Kadayam Viswanathan, Sharon, MA (US); Shin Utsuzawa, Sugar Land, TX (US); Kamilla Fellah, Somerville, MA (US); Shawn David Taylor, Reading, MA (US); MaryEllen Loan, Quincy, MA (US); Paul Ryan Craddock, Scituate, MA (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 18/056,373

(22) Filed: Nov. 17, 2022

(65) Prior Publication Data

US 2023/0078728 A1 Mar. 16, 2023

Related U.S. Application Data

(62) Division of application No. 16/969,209, filed as application No. PCT/US2019/017408 on Feb. 11, 2019, now Pat. No. 11,519,266.

(Continued)

(51) Int. Cl.
*E21B 49/02* (2006.01)
*E21B 49/00* (2006.01)

(Continued)

(52) U.S. Cl.
CPC ............ *E21B 49/02* (2013.01); *E21B 49/005* (2013.01); *G01V 3/32* (2013.01); *G01V 3/38* (2013.01); *G01R 33/44* (2013.01)

(58) Field of Classification Search
CPC ......... E21B 49/02; E21B 49/005; G01V 3/32; G01V 3/38; G01R 33/44; G01R 33/448;

(Continued)

(56) References Cited

U.S. PATENT DOCUMENTS 4,389,613 A * 6/1983 Brown ..................... G01V 3/32
324/303
4,413,512 A * 11/1983 Zemanek, Jr. ........... G01V 3/14
324/303

(Continued)

FOREIGN PATENT DOCUMENTS

WO 2013155508 A1 10/2013
WO 2017048737 A1 3/2017

OTHER PUBLICATIONS

Kausik et al., "Novel Reservoir Quality Indices for Tight Oil", SPE 178622, Unconventional Resources Technology Conference, Jul. 2015 10 pages.

(Continued)

*Primary Examiner* — G. M. A Hyder
(74) *Attorney, Agent, or Firm* — Jeffrey D. Frantz

(57) ABSTRACT

Methods and systems are provided that combine NMR and IR spectroscopy measurements on a rock sample to determine data representing at least one property of the rock sample. In one embodiment, cuttings can be split into first and second lots. Results of an NMR measurement performed on the first lot of cuttings without cleaning can be analyzed to determine pore volume of the cuttings. Results of an IR spectroscopy measurement performed on the second lot of cuttings after solvent cleaning can be analyzed to determine matrix density of the cuttings. Porosity can be (Continued)

determined from the pore volume and matrix density of the cuttings. In another embodiment, combined NMR and IR spectroscopy measurements can be performed on an unprepared rock sample (without solvent cleaning) to characterize properties of kerogen in the rock sample and porosity. In another aspect, a method is provided that employs multinucleic NMR measurements to determine porosity.

4 Claims, 20 Drawing Sheets

Related U.S. Application Data

(60) Provisional application No. 62/629,484, filed on Feb. 12, 2018.

(51) Int. Cl.
*G01V 3/32* (2006.01)
*G01V 3/38* (2006.01)
*G01R 33/44* (2006.01)

(58) Field of Classification Search
CPC .............. G01N 21/3563; G01N 33/241; G01N 24/082; G01N 24/081; G01N 24/08
See application file for complete search history.

(56) References Cited

U.S. PATENT DOCUMENTS

| | | | |
|---|---|---|---|
| 8,906,690 | B2 | 12/2014 | Pomerantz |
| 8,967,249 | B2 | 3/2015 | Akkurt et al. |
| 2006/0181274 | A1* | 8/2006 | Freedman ................ G01V 3/32 324/306 |
| 2010/0057409 | A1 | 3/2010 | Jones et al. |
| 2013/0269420 | A1 | 10/2013 | Valenza et al. |
| 2013/0269933 | A1 | 10/2013 | Pomerantz et al. |
| 2015/0022202 | A1 | 1/2015 | Song et al. |
| 2016/0061803 | A1 | 3/2016 | Hadj-Sassi et al. |
| 2016/0108687 | A1 | 4/2016 | Rapoport |
| 2017/0248011 | A1 | 8/2017 | Craddock et al. |
| 2018/0188161 | A1 | 7/2018 | Craddock et al. |
| 2020/0408090 | A1 | 12/2020 | Kadayam Viswanathan et al. |
| 2021/0116335 | A1* | 4/2021 | Althaus ................ E21B 49/005 |

OTHER PUBLICATIONS

Jiang et al., "Integrated Petrophysical Interpretation of Eagle Ford Shale with 1-D and 2-D Nuclear Magnetic Resonance (NMR)", Society of Petrophysicists and Well-Log Analysis SPWLA 54th Annual Logging Symposium, Jun. 22-26, 2013, 22 pages.

Kausik et al., "NMR Petrophysics for Tight Oil Shale Enabled by Core Resaturation", SCA2014-073, International Symposium of the Society of Core Analysis, Avignon, France, 2014, 6 pages.
Search Report and Written Opinion of International Patent Application No. PCT/US2019/017408 issued on May 27, 2019; 13 pages.
Kausik et al., "NMR Relaxometry in Shale and Implications for Logging", Petrophysics, 2016, vol. 57, No. 4, pp. 339-350.
Kausik et al., "High-and Low-Field NMR Relaxometry and Diffusometry of the Bakken Petroleum System", Petrophysics, 2017, vol. 58, No. 4, pp. 341-351.
Santarelli et al., "Formation Evaluation from Logging on Cuttings", Society of Petroleum Engineers Reservoir Evaluation & Engineering, 1998, pp. 238-244.
Herron et al., "Kerogen Content and Maturity, Mineralogy and Clay Typing from DRIFTS Analysis of Cutting or Core", Petrophysics, vol. 55, No. 5, pp. 435-446, 2014.
Loan et al., "Rapid Quantification of Mineralogy, Organic Matter, and Thermal Maturity of Cuttings with Diffuse Reflectance infrared Fourier Transform Spectroscopy (DRIFTS): a Permian Basin Case Study", Presented at the Unconventional Resources Conference and Exhibition, Austin, Texas Jul. 24-26, 2017, 12 pages.
Mitchell et al., "Low-field permanent magnets for industrial process and quality control", Prog. Nucl. Magn. Reson. Spectros. 76, 1-60, 2014.
Hoult and Richards, "The signal-to-noise ratio of the nuclear magnetic resonance experiment", J. Magn. Reson. 24, 71-85, 1976.
Mitchell et al., "Nuclear magnetic resonance relaxation and diffusion in the presence of internal gradients: the effect of field strength", Phys. Rev. E 81, 026101, 2010.
Hürlimann et al., "Spin echoes in a constant gradient and in the presence of simple restriction", J. Magn. Reson. Ser. A 113, 260, 1995.
Mitchell et al., "Contributed Review: Nuclear magnetic resonance core analysis at 0.3", T Rev. Sci. Instrum. 85, 111502, 2014.
Extended European Search Report issued in European Patent Application No. 19750923.5 dated Oct. 15, 2021, 6 bages.
Craddock et al., Kerogen Thermal Maturity and Content of Organic-Rich Mudrocks Determined Using Stochastic Linear Regression Models Applied to Diffuse Reflectance 1 R Fourier Transform Spectroscopy (DRI FTS), Organic Geochemistry, 110 (2017) 122-133, 2017.
Witte et al., Structural Modifications of Kerogen During Natural Evolution as Derived from 13C CP/MAS N M R, 1 R spectroscopy and Rock-Eval Pyrolysis of Toarcian Shales, Organic GeoChemistry, vol. 13, Issues 4-6, 1039-1044, 1988.
Mitchell et al., Evaluation of Production Log Data from Horizontal Wells Drilled in Organic Shales, SPE-144326-MS, North American Unconventional Gas Conference and Exhibition, Jun. 14-16, 2011, 23 pages.

* cited by examiner

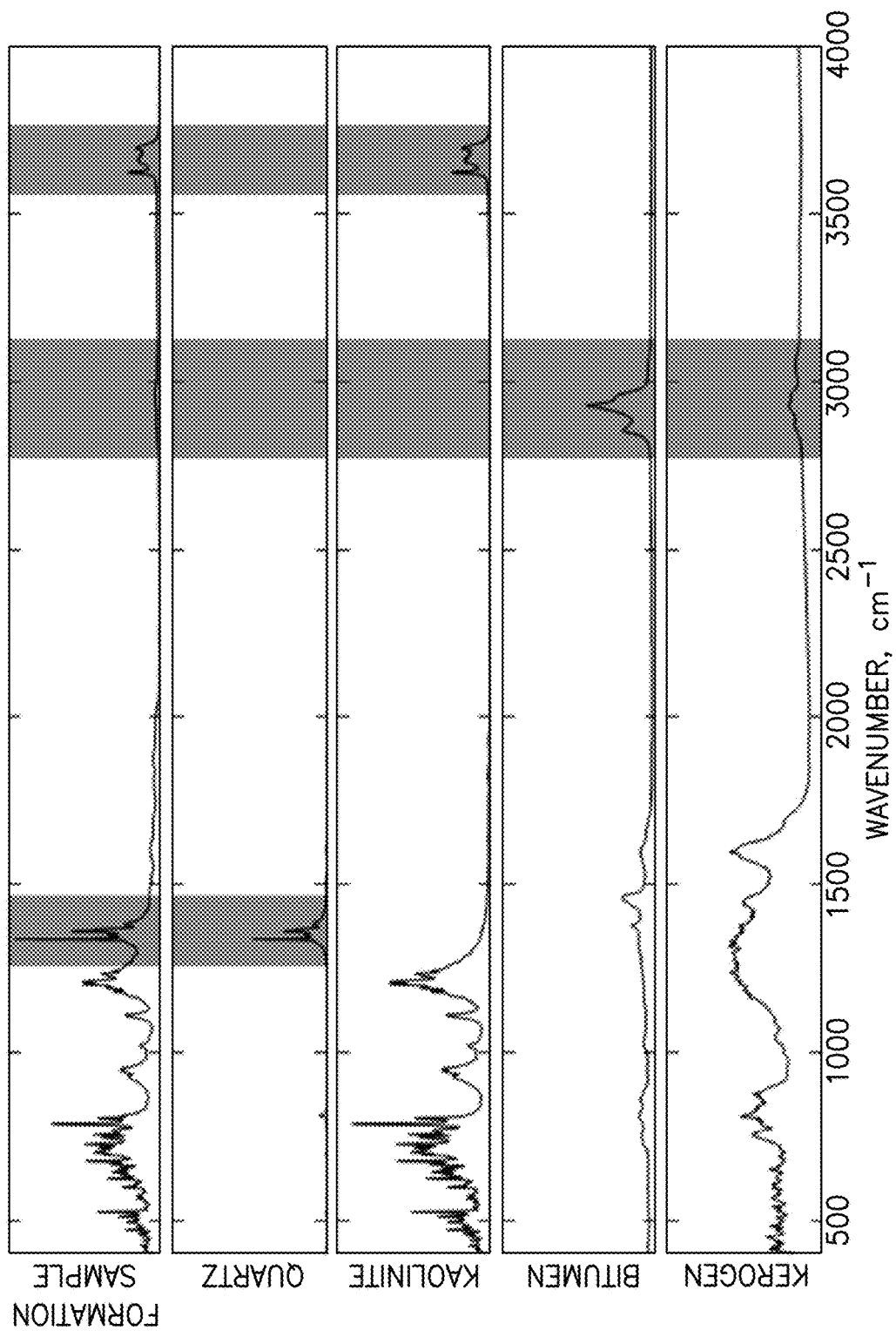

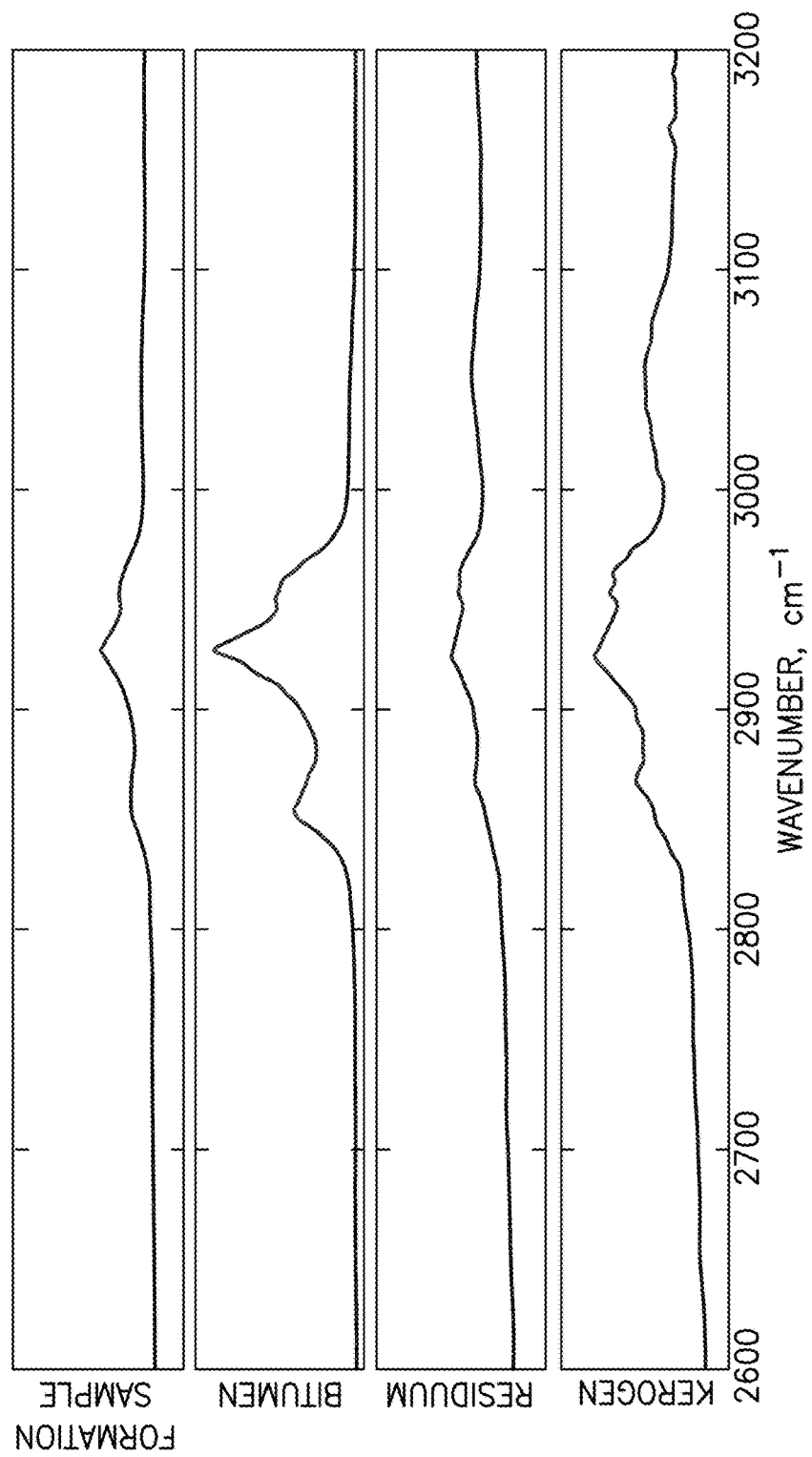

METHODS AND SYSTEMS FOR CHARACTERIZING PROPERTIES OF RESERVOIR ROCK

CROSS-REFERENCE TO RELATED APPLICATION(S)

This application is a division of U.S. patent application Ser. No. 16/969,209 with a filing date of Aug. 12, 2020, which is the U.S. National Phase of International Patent Application No. PCT/US2019/017408 filed on Feb. 11, 2019, which claims priority from U.S. Provisional Application No. 62/629,484, filed Feb. 12, 2018, herein incorporated by reference in its entirety.

FIELD

This application relates to methods and apparatus to characterize subterranean formations. Specifically, embodiments described herein relate to collection, preparation, and analysis of properties of rock of a subterranean formation.

BACKGROUND

Reservoir quality is largely controlled by reservoir parameters such as porosity, hydrocarbon saturation, permeability, mineralogy and thermal maturity. Generally, high vertical resolution log measurements and core analysis can provide accurate reservoir parameters for assessing reservoir quality in vertical wells. Similar technologies can be extended to characterize reservoir parameters for assessing reservoir quality in highly-deviated production wells for unconventional plays, including the conveyance of traditional wireline tools, measurements behind the bit, and measurements collected by passing the tool through the bit. However, the length and conditions of these highly-deviated wells makes these measurements challenging and not economically viable, resulting in most lateral wells not being logged or logged only with gamma ray (GR) tools. Instead, multiple vertical wells are placed across the extent of the basin and formation properties, such as bed boundaries, pinch-out points, porosity, mineralogy, and organic-matter content, are determined and assumed to be linearly uniform. Depending on the unconventional play, this indirect method of reservoir characterization may fail to capture the variation in porosity and fluid types, insoluble hydrocarbon (kerogen) concentrations, mineralogy, and clay-type and clay-volumes that impact reservoir quality laterally. Without a record of the well obtained by logs, little information is available in the event of poor production of a lateral well after drilling and completion.

Completion quality is an engineering assessment of factors that determine the effectiveness of stimulation treatments (particularly hydraulic fracture treatments) in unconventional reservoirs, and includes the ability to initiate and create an induced fracture network, the degree of reservoir contact of the newly created fractures, the level of connection to the natural fracture system of those created fractures and ability of the stimulated reservoir to deliver gas or oil into the well. Important inputs to the derivation of completion quality include the rock's mineralogy, porosity, mechanical properties, compressive strength and tensile strength. In addition, the presence and state of natural fractures, the in-situ stresses and the formation pore pressure can also be provided as inputs to the derivation of completion quality.

Nuclear Magnetic Resonance ("NMR") relaxometry has been gaining ground as a reliable approach to core analysis due to its capabilities to characterize fluids in reservoir rocks and measure them quantitatively. The NMR relaxometry measurements yield fluid types and wettability non-destructively and in a relatively quick fashion. These aid in assessing reservoir quality and reserve estimates and in core-log correlations. The porosities derived from the NMR log have been shown to compare favorably to the measured core porosities and to represent the potentially producible fluid fractions and/or the fluids fractions contained within the rock sample. NMR laboratory measurements are typically made at frequencies similar to the NMR logging tools (~2 MHz), on 1.5"×1.5" rock core samples that are trimmed and surface ground to fit in the NMR probe, resulting in a high filling factor of the radio frequency (RF) probe to achieve optimum signal-to-noise ratios (SNR). The $^1$H (proton) NMR measurements are mainly used to obtain the volumes of the fluids in the pores (pore volume). When combined with the bulk volumes measured using calipers on regular shaped cores, porosity can be calculated.

Although the value of NMR measurements of unconventional shale rocks has been shown on cores and logs in vertical pilot wells, the absence of routine logs and reliable core measurements from horizontal wells make it challenging to obtain a more complete understanding of unconventional reservoirs.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In embodiments, methods and systems are provided for characterizing properties of a rock sample obtained from a subterranean formation, which involve performing an NMR measurement on the rock sample, performing an IR spectroscopy measurement on the rock sample, and using results of the NMR measurement and results of the IR spectroscopy measurement to determine data representing at least one property of the rock sample.

In embodiments, the IR spectroscopy measurement can be a DRIFTS spectroscopy measurement or other IR spectroscopy measurement.

In embodiments, the rock sample can be a core plug, cuttings, and some other rock sample form.

In one embodiment, the rock sample can be cuttings formed by drilling operations that use oil-based drilling fluid. The cuttings are obtained from the subterranean formation and split to provide a first lot of cuttings separate and distinct from a second lot of cuttings. An NMR measurement is performed on the first lot of cuttings without cleaning the first lot of cuttings with a solvent that would remove certain organic components from the first lot of cuttings. An IR spectroscopy measurement is performed on the second lot of cuttings after cleaning the second lot of cuttings with a solvent that removes certain organic components from the second lot of cuttings. The results of the NMR measurement performed on the first lot of cuttings can be analyzed to determine data characterizing pore volume of the cuttings obtained from the subterranean formation. The results of the IR spectroscopy measurement performed on the second lot of cuttings can be analyzed to determine data characterizing matrix density of the cuttings obtained from the subterranean formation. Data representing bulk volume of the cuttings obtained from the subterranean formation can be calculated based on the pore volume data and the matrix density data of the cuttings. And data representing porosity of the cuttings obtained from the subterranean formation can be calculated based on the pore volume data and the bulk volume data of the cuttings.

In another embodiment, results of the NMR measurement performed on the rock sample can be analyzed to determine data representing mass fractions of certain organic components in the rock sample. Results of the IR spectroscopy measurement performed on the rock sample can be analyzed in conjunction with the data representing mass fractions of certain organic components in the rock sample as determined from the NMR measurement to obtain data representing a residuum IR spectrum representative of kerogen in the rock sample. The data representing the residuum IR spectrum can be processed to generate data that characterizes properties (such as thermal maturity or kerogen density) of kerogen in the rock sample.

In one embodiment, the data representing mass fractions of certain organic components (such as oil and bitumen and possibly others) in the rock sample can be determined from the NMR measurement by obtaining data representing a T1-T2 distribution of the rock sample, processing the data representing the T1-T2 distribution to obtain data representing volumes for the certain organic components, and using the data representing volumes for the certain organic components and mass of the rock sample to compute the data representing mass fractions of certain organic components. The data representing the residuum IR spectrum can be determined by using the data representing mass fractions of the certain organic components as determined from the NMR measurement to subtract contribution of the certain organic components (such as oil and bitumen) from a measured IR spectrum.

In embodiments, the IR spectroscopy measurement can be performed on cuttings that are cleaned to remove contaminants and certain organic components from the cuttings. For example, the cuttings can be rinsed with a base oil or clean drilling fluid (such as diesel) to remove contaminants and wash away mobile hydrocarbon components from the cuttings. Then, the cuttings can be heated in an oven to evaporate hydrocarbon components (such as solvents or naturally occurring mobile hydrocarbon components) from the cuttings. Then, the cuttings can be washed with soapy water to remove residual hydrocarbon components (i.e., solvent, drilling fluid, naturally occurring mobile hydrocarbon components) from the cuttings and then dried. Then, the cuttings can be cleaned with a solvent (such as pentane) to remove certain organic components from the cuttings. The cuttings can also be crushed to reduce cutting size and thereafter cleaned with a solvent (such as pentane) to remove certain organic components from the crushed cuttings. Such cleaning can be carried out over a vacuum filter and/or at elevated temperature and pressure.

In yet another aspect, a method is provided that employs multi-nucleic NMR measurements to determine porosity of a rock sample. The method involves three different calibration NMR measurements. A first calibration NMR measurement is performed on a known-volume of a first fluid that contains hydrogen nuclei, wherein the first calibration NMR measurement is performed at a first frequency for measuring hydrogen nuclei in the first fluid. A second calibration NMR measurement is performed on a known-volume of a second fluid that contains non-hydrogen nuclei, wherein the second calibration NMR measurement is performed at a different second frequency for measuring non-hydrogen nuclei in the second fluid. A third calibration NMR measurement is performed on a sample holder filled with the second fluid, wherein the third calibration NMR measurement is performed at the second frequency. The rock sample (e.g., cuttings) is added to a sample holder filled with the second fluid. An NMR measurement is performed on the sample holder filled with the second fluid and the rock sample, wherein the NMR measurement is performed at the second frequency. The results of the NMR measurement performed at the second frequency, the results of the third calibration NMR measurement, the results of the second calibration NMR measurement and the known-volume of the second fluid are processed to determine data representing bulk volume of the rock sample. Another NMR measurement is performed on the sample holder filled with the second fluid and the rock sample at the first frequency. The results of the NMR measurement performed at the first frequency, the results of the first calibration NMR measurement, and the known-volume of the first fluid are processed to determine data representing pore volume of the rock sample. Data representing porosity of the rock sample can be determined based on the bulk volume data and the pore volume data of the rock sample.

In embodiments, the first fluid can be a hydrogen-based fluid (such as water or heavy water), the second fluid can be a fluorine-based fluid (such as a fluorocarbon), and the second frequency can be selected for measuring fluorine nuclei in the fluorine-based fluid.

In embodiments, a maximum signal amplitude that results from the NMR measurement performed at the second frequency can be subtracted from a maximum signal amplitude that results from the third calibration NMR measurement to determine data characterizing a difference in signal amplitude, where such data is divided by data representing a maximum signal amplitude that results from the second calibration NMR measurement and multiplied by data representing the known-volume of the second fluid to determine the data representing bulk volume of the rock sample. Furthermore, a maximum signal amplitude that results from the NMR measurement performed at the first frequency can be divided by data representing a maximum signal amplitude that results from the first calibration NMR measurement and multiplied by data representing the known-volume of the first fluid to determine the data representing pore volume of the rock sample.

BRIEF DESCRIPTION OF THE DRAWINGS

FIG. 12A-12E illustrate the DRIFT spectra of a formation sample and several discrete and identifiable components of the formation sample, including mineral components such as quartz (characteristic vibration modes between approximately 1200 and 1400 $cm^{-1}$) and kaolinite (characteristic vibration modes between approximately 3600 and 3750 $cm^{-1}$), and organic matter such as bitumen and kerogen (characteristic vibration modes between approximately 1400 and 750 $cm^{-1}$ and between approximately 2800 and 3100 $cm^{-1}$).

FIGS. 13A-13D illustrate exemplary DRIFT spectra measured by the workflow of FIGS. 11A-11C in the region of the IR spectrum between 2600 and 3200 $cm^{-1}$ wherein are expressed prominent IR absorption bands associated with C—H vibrational modes in organic matter.

DESCRIPTION

Figure 1:
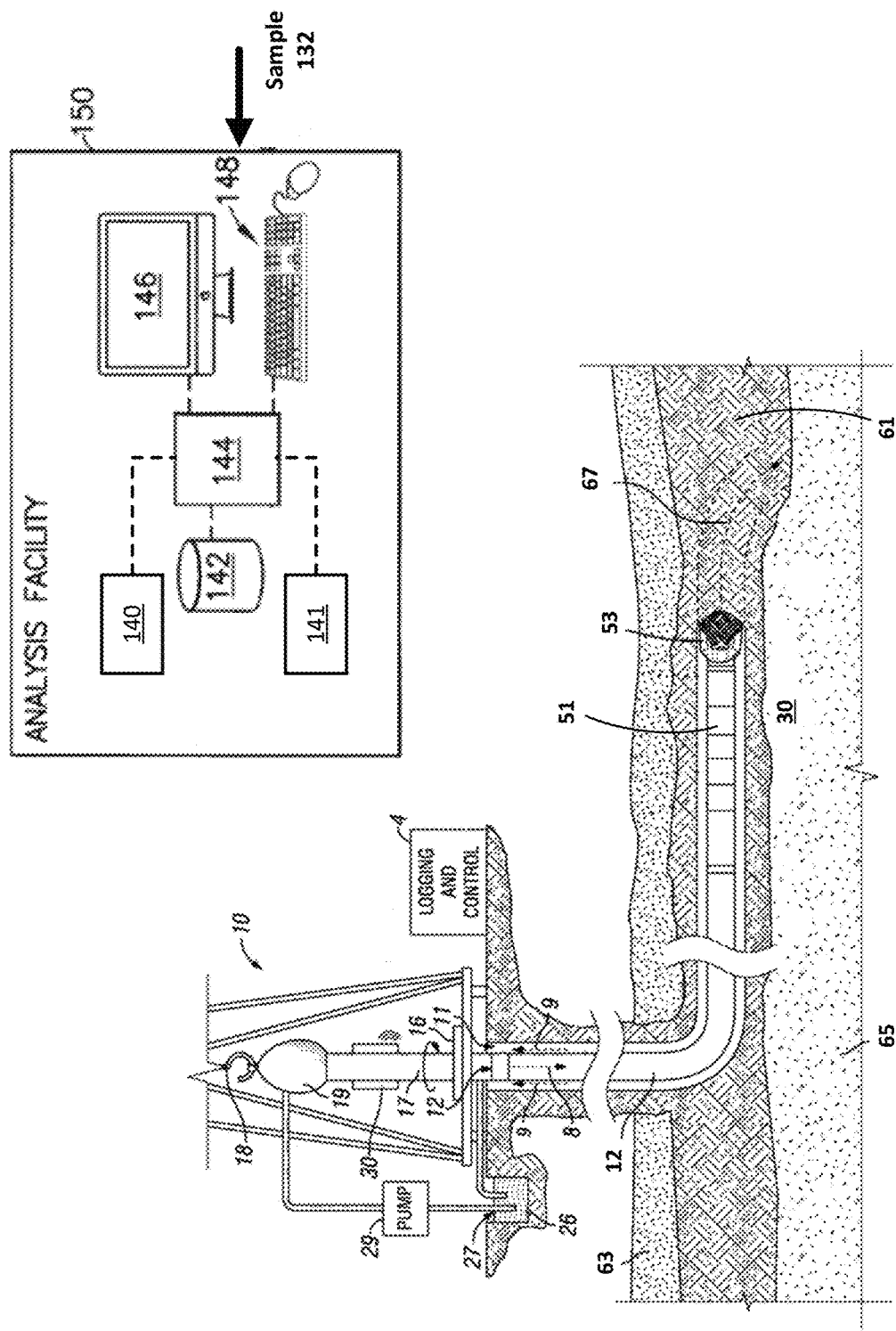
FIG. 1 is a schematic diagram illustrating a drilling tool drilling a wellbore and an analysis facility, according to some embodiments.

The discussion below is directed to certain implementations and/or embodiments. It is to be understood that the discussion below may be used for the purpose of enabling a person with ordinary skill in the art to make and use any subject matter defined now or later by the patent "claims" found in any issued patent herein.

It is specifically intended that the claimed combinations of features not be limited to the implementations and illustrations contained herein but include modified forms of those implementations including portions of the implementations and combinations of elements of different implementations as come within the scope of the following claims. It should be appreciated that in the development of any such actual implementation, as in any engineering or design project, numerous implementation-specific decisions may be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the claimed invention unless explicitly indicated as being "critical" or "essential."

It will also be understood that, although the terms first, second, etc. may be used herein to describe various elements, these elements should not be limited by these terms. These terms may be used to distinguish one element from another. For example, a first object or step could be termed a second object or step, and, similarly, a second object or step could be termed a first object or step, without departing from the scope of the disclosure. The first object or step, and the second object or step, are both objects or steps, respectively, but they are not to be considered a same object or step.

The term "reservoir quality" or "RQ" is defined by a number of petrophysical and hydrocarbon properties (e.g., porosity, permeability, total organic content or TOC, total inorganic content or TIC, maturation, hydrocarbon content and type, gas sorption mechanisms) that define reservoir potential. The term "completion quality" or "CQ" depends on the poromechanical properties of the field and reservoir, which means the conditions that are favorable to the creation, propagation and containment of hydraulic fractures, as well as the placement of proppant and retention of fracture conductivity. It depends mainly on the intrinsic geomechanics properties, i.e., in situ stress field, pore pressure, material properties (elastic, yield or quasi-brittle failure, hardness, rock-fluid sensitivity), their anisotropic nature and their spatial heterogeneities, as well as the presence of discontinuities (such as natural fractures or geological layering) and the orientation of the well.

Further, as a well is being drilled, the rock that is being drilled is cut or otherwise fragmented by the drill bit into small pieces, called "cuttings", that are removed from the bulk of the formation via drilling fluid. The cuttings are carried to the surface by the drilling fluid and can be screened out of the drilling fluid and collected without interfering with the drilling operations. The cuttings are representative of the reservoir rock—although they have been altered by the drilling process, they still provide an understanding of the properties of the reservoir rock. This is often referred to as "mud logging" or "cuttings evaluation." For effective logging or evaluation as described below, in some embodiments, the cuttings are prepared by removing residual drilling fluids.

The term "unconventional" is used to refer to a formation where the source and reservoir are the same, and stimulation (such as hydraulic fracturing) is required to create production. The term "source" implies that the formation contains appreciable amounts of organic matter, which through maturation or biological processes has generated hydrocarbons (gas or oil, as in Barnett and Eagle Ford, respectively). The term "reservoir" signifies that the hydrocarbons have not been able to escape and are trapped in the same space (or very near) where they were generated. Unconventional formations can have extremely low permeabilities, (mainly in the order of nanodarcies), which explains why stimulation is needed.

The terms "bitumen" and "kerogen" are non-mobile, organic parts of shales. "Bitumen" is defined as the fraction that is soluble in a solvent (typically a polar solvent such as chloroform or a polarizable solvent such as benzene). "Kerogen" is defined as the fraction that is insoluble in the solvent.

The term "rock core" is a reservoir rock sample collected with a special tool that extracts large samples with little exposure to drilling fluids.

The embodiments described herein relate to the field of geomechanics and its application to the oil and gas industry. Geomechanics is an integrated domain linking in situ physical measurements of rock mechanical properties via wellbore logging or wellbore drilling, in situ hydraulic measurements of in situ pore pressure and stress field, surface laboratory measurements on cores to engineering practices for drilling, fracturing and reservoir purposes via the construction of integrated earth models, and modeling tools and workflows.

In embodiments described herein, an NMR measurement can be performed on cuttings. The results of the NMR relaxometry measurements can be used to characterize properties of the cuttings, such as pore volume, pore fluid saturations and pore fluid type. The NMR measurement can be performed on the cuttings without cleaning the cuttings with a solvent that removes organic components (such as oil-based components that originate from an oil-based drilling fluid or additives).

Furthermore, the pore volume obtained from the NMR measurement performed on the cuttings can be combined with rock properties obtained from a spectroscopy measurement (such as diffuse reflectance infrared Fourier-transform spectroscopy or DRIFTS measurement) performed on cleaned cuttings to characterize porosity of the cuttings (and thus porosity of the drilled formation rock from which they originate) and possibly other useful reservoir parameters.

To clean the cuttings for the spectroscopy measurement, the cuttings can be immersed or otherwise exposed to a solvent that removes soluble organic components, such as oil-based drilling fluids and additives, oil and bitumen. After such cleaning, the cuttings can be dried. Thereafter, insoluble organic components (i.e., kerogen) can remain in the cuttings with little or no soluble organic components. Thus, information regarding the inorganic mineral components and the insoluble organic components (i.e., kerogen) of the cuttings remain, while information regarding the soluble organic components and porosity of the cuttings is lost. To accommodate for the loss of such information, the workflow combines the pore volumes obtained from the NMR measurement with rock properties obtained from the spectroscopy measurement to characterize porosity of the cuttings and possibly other useful reservoir parameters.

Note that porosity measurements from cuttings require a reliable measurement of bulk volume. Typically, bulk volume is determined by measuring the sample mass and grain density (which can be measured by helium pycnometer or calculated from mineralogy). But these additional measurements require time-consuming sample cleaning procedures making them improbable for wellsite applications. In embodiments, the spectroscopy measurement performed on the cuttings can be used to determine bulk volume.

The results of the workflow can be provided quickly and efficiently. Furthermore, the results can provide a valuable source of information on the geology of the formation and reservoir quality, specifically providing an accurate indication of reservoir quality of lateral wells in an otherwise data poor environment. Furthermore, the cuttings can be correlated with depth in the wellbore and can help with understanding formation stratigraphy and finding pay zones. Furthermore, the results can provide a quantitative measure of porosity as well as the different fractions (namely kerogen, bitumen and liquid hydrocarbon, free water, and bound water) that occupy the pore space of the reservoir rock, which can be very useful to understand the reservoir and design and optimize completion of the well that traverses the reservoir.

FIG. 1 illustrates a wellsite system in which the disclosed methods and systems can be employed. The wellsite system can be onshore or offshore. In this exemplary system, a wellbore 11 is formed in a subsurface formation 30 by directional rotary drilling in a manner that is well known. A drill string 12 is suspended within the wellbore 11 and has a bottom hole assembly 51 which includes a drill bit 53 at its lower end. The surface system includes platform and derrick assembly 10 positioned over the wellbore 11, the assembly 10 including a rotary table 16, kelly 17, hook 18 and rotary swivel 19. The drill string 12 is rotated by the rotary table 16, energized by means not shown, which engages the kelly 17 at the upper end of the drill string 12. The drill string 12 is suspended from a hook 18, attached to a traveling block (also not shown), through the kelly 17 and a rotary swivel 19 which permits rotation of the drill string 12 relative to the hook 18. As is well known, a top drive system could alternatively be used.

In the example of this embodiment, the surface system further includes drilling fluid or mud 26 stored in a pit 27 formed at the wellsite. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 53, and then circulates upwardly through the annulus region between the outside of the drill string and the wall of the wellbore 11, as indicated by the directional arrows 9. In this well-known manner, the drilling fluid lubricates the drill bit 53 and carries cuttings up to the surface as the drilling fluid is returned to the pit 27 for recirculation.

As is known in the art, sensors may be provided about the wellsite to collect data, preferably in real time, concerning the operation of the wellsite, as well as conditions at the wellsite. For example, such surface sensors may be provided to measure parameters such as standpipe pressure, hook load, depth, surface torque, rotary rpm, among others.

The bottom hole assembly 51 can include sensors or modules (such as one or more logging-while drilling modules or one-more more measurement-while-drilling (MWD) modules) and a rotary steerable system that controls the drilling direction of the drill bit 53. For example, one or more LWD modules of the bottom-hole assembly 51 can include capabilities for measuring and storing directional electromagnetic response data that is sensitive to resistivity profile of the formation in the vicinity of the bottom hole assembly 51, and one or more MWD modules can include capabilities for measuring, processing, and storing information that characterizes a position and direction of the drill string 12 and the drill bit 53 as well as other drilling measurements, such as a weight-on-bit, torque, and shock and/or vibration. As used herein, the term "module" as applied to LWD and MWD devices is understood to mean either a single tool or a suite of multiple tools contained in a single modular device.

The bottom hole assembly 51 can also include a downhole telemetry subsystem that communicates data signals and control signals between the components of the bottom hole assembly 51 and a surface-located logging and control unit 4. The downhole telemetry subsystem can employ a variety of telemetry methods, such as wired telemetry methods (e.g., drill pipe that incorporate telemetry cables or fiber optic cables) and wireless telemetry method (e.g., mud-pulse telemetry methods, electromagnetic telemetry methods, and acoustic telemetry methods). The downhole telemetry subsystem can also supply electrical power supply signals generated by a surface-located power source for supply to the components of the bottom hole assembly 51. The bottom hole assembly 51 can also include a power supply transformer/regulator for transforming the electric power supply signals supplied by the surface-located power source to appropriate levels suitable for use by the components of the bottom hole assembly 51. In alternate embodiments, the bottom hole assembly 51 can include an apparatus for generating electrical power for supply to the components of the bottom hole assembly 51, such as a mud turbine generator powered by the flow of the drilling fluid. Other power and/or battery systems may be employed.

The surface-located logging and control unit 4 (and possibly other computer systems remotely coupled thereto via a data communication network) can cooperate with the rotary steerable system of the bottom hole assembly 51 to provide geo-steering control of the drilling direction of the drill bit 53. As shown in FIG. 1, the wellbore 11 has been directionally drilled to enter an unconventional formation reservoir 61 disposed between an upper formation layer 63 and a lower formation layer 65 in the formation 30. The planned wellbore trajectory is shown by arrow 67.

Rock samples 132 from the reservoir 61 (such as cuttings collected from the drilling fluid 26 that returns from the wellbore 11) can be collected and transported to a surface-located analysis facility 150. Note that the analysis facility 150 can be located at the wellsite or it can be located remotely from the wellsite. The analysis facility 150 includes an NMR apparatus 140, a spectrometer 141, one or more central processing units 144, storage system 142, a user display 146 and a user input system 148. The storage system 142 can be in the form of magnetic storage, such as a hard disk, and/or in the form of solid-state memory such as flash memory but is not limited to these two. The NMR apparatus 140 can be configured to conduct NMR measurements on the rock samples 132 and the spectrometer can be configured to conduct spectroscopy measurements on the rock samples 132. The results of these measurements can be used to characterize properties of the rock samples as described herein.

Figure 2:
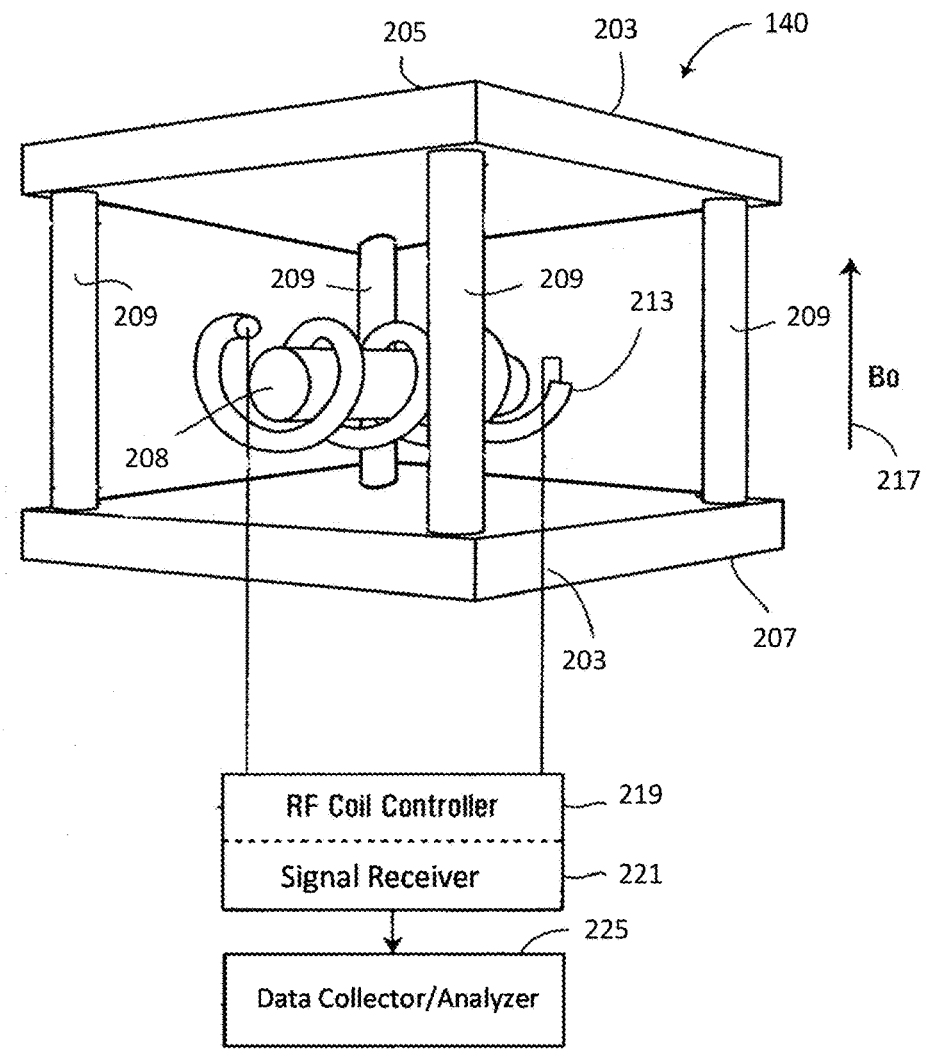
FIG. 2 is a schematic diagram of an exemplary NMR apparatus, according to some embodiments.

FIG. 2 shows a schematic diagram of an exemplary NMR system 140 that can be part of the analysis facility 150 and configured to conduct NMR measurements on rock samples (e.g., cuttings). The NMR system 140 includes a permanent magnet having spaced-apart magnetic pole pieces 205, 207, spacers (e.g., pillars) 209 separating the magnetic pole pieces 205, 207, and an RF coil 213 which is configured to receive a sample holder 208 that contains a rock sample. The arrow 217 shows the direction of the magnetic field, B0. Connectors 203 provide for electrical connection of the RF coil 213 to control circuitry as described below.

The NMR system 140 further includes an RF coil controller 219 for generating and delivering RF excitation pulses to the RF coil 213 for transmission into the space occupied by the rock sample as part of the NMR measurements, and a signal receiver 221 for receiving an NMR signal detected by the RF coil 213 as part of such NMR measurements. The NMR system 140 further includes a data collector/analyzer 225 for receiving data from the signal receiver 221 and data storage. The signal receiver 221 generates a signal or data which represents the NMR signal detected by the RF coil 213 and supplies such signal to the data collector/analyzer 225 for processing.

Figure 3:
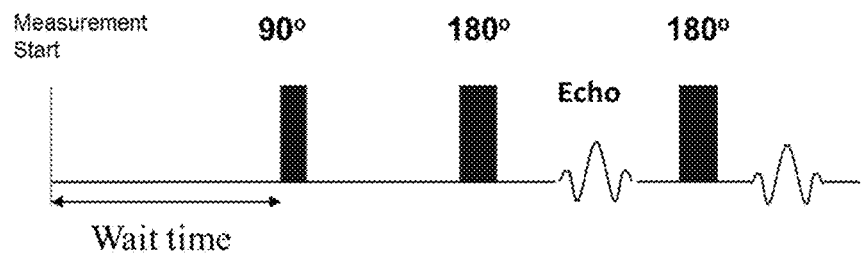
FIG. 3 is a schematic diagram of an exemplary CPMG pulse sequence that can be used by the NMR apparatus of FIG. 2 for NMR measurements, according to some embodiments.

The NMR measurements can use specially designed data acquisition schemes (called NMR pulse sequences) which describe the timings of transmission and reception of electromagnetic signals. The NMR pulse sequence for the measurement of a $T_2$ relaxation time distribution is called the CPMG echo train and is shown in FIG. 3. The CPMG echo train includes an initial idle time or wait time to allow the nuclei in the fluids contained in the rock sample to come to equilibrium with the magnetic field induced by the permanent magnet of the NMR system. Thereafter, a series of radio-frequency pulses are applied to the space occupied by the rock sample using the RF coil 213. The time between the adjacent 180-degree RF pulses is the echo spacing, TE. The initial wait time is often long enough to fully polarize the system. Midway between the 180-degree RF pulses, NMR signals called echoes are detected by the RF coil 213. The amplitude of the echoes decay or attenuate with time. The data collector/analyzer 225 (or some other data processor) can be configured to obtain a $T_2$ distribution by fitting the echo amplitudes to a multi-exponential model as follows.

In such an experiment, a train of echo signal is acquired. The signal amplitude, S, is measured as a function of the echo time, $t_{echo}$, which is the time of the echo from the beginning of the first 90-degree pulse and given by:

$$t_{echo} = n*TE, \qquad \text{Eqn. (1)}$$

where n is the number of echo, and TE is the echo spacing or time between two adjacent 180-degree pulses.

The signal amplitude $S(t_{echo})$ at a given echo time $t_{echo}$ then follows an exponential decay form given by:

$$S(t_{echo}) = S(0)\exp\left(-n*\frac{TE}{T_2}\right), \qquad \text{Eqn. (2)}$$

for a rock sample with a single $T_2$ component.

For many rock samples where a number of different $T_2$ components are present, the signal amplitude $S(t_{echo})$ at a given echo time $t_{echo}$ is a sum of all $T_2$ components, which is given by an integral over a range of $T_2$ values as follows:

$$S(t_{echo}) = \int dT_2 f(T_2)\exp\left(-n*\frac{TE}{T_2}\right), \qquad \text{Eqn. (3)}$$

where $f(T_2)$ is the $T_2$ distribution function.

Inversion processing can be used to solve for the $T_2$ distribution function $f(T_2)$ that fits the signal amplitude $S(t_{echo})$ measured for the echo times. The $T_2$ values of the $T_2$ distribution function $f(T_2)$ less than a $T_2$cutoff (corresponding to pores filled with bound water) can be integrated to provide data describing pore volume of the sample. This pore volume corresponds to the pore space of the rock sample that holds producible fluids (e.g., free water, mud filtrates, oil, and gas).

In other embodiments, other types of NMR analysis can be used to determine pore volume. For example, the NMR analysis can solve for a distribution function of spin-lattice $T_1$ relaxation times, and the pore volume can be determined from such distribution function. In another example, diffusion-edited NMR pulse sequences can be used to solve for distribution functions of $T_1$ or T2 relaxation times for different fluid components, and the pore volumes for the different fluid components can be determined from such distribution functions. In this case, the pore volume of the sample can be determined by adding together the pore volumes for the different fluid components.

The 2D $T_1T_2$ NMR measurements can be used to identify and separate bitumen and clay bound water, fluids in organic and inorganic porosity, and free fluids. At higher fields, kerogen can be identified due to the differences in T1 and therefore NMR provides a nondestructive method for fluid typing in rocks.

Figure 4:
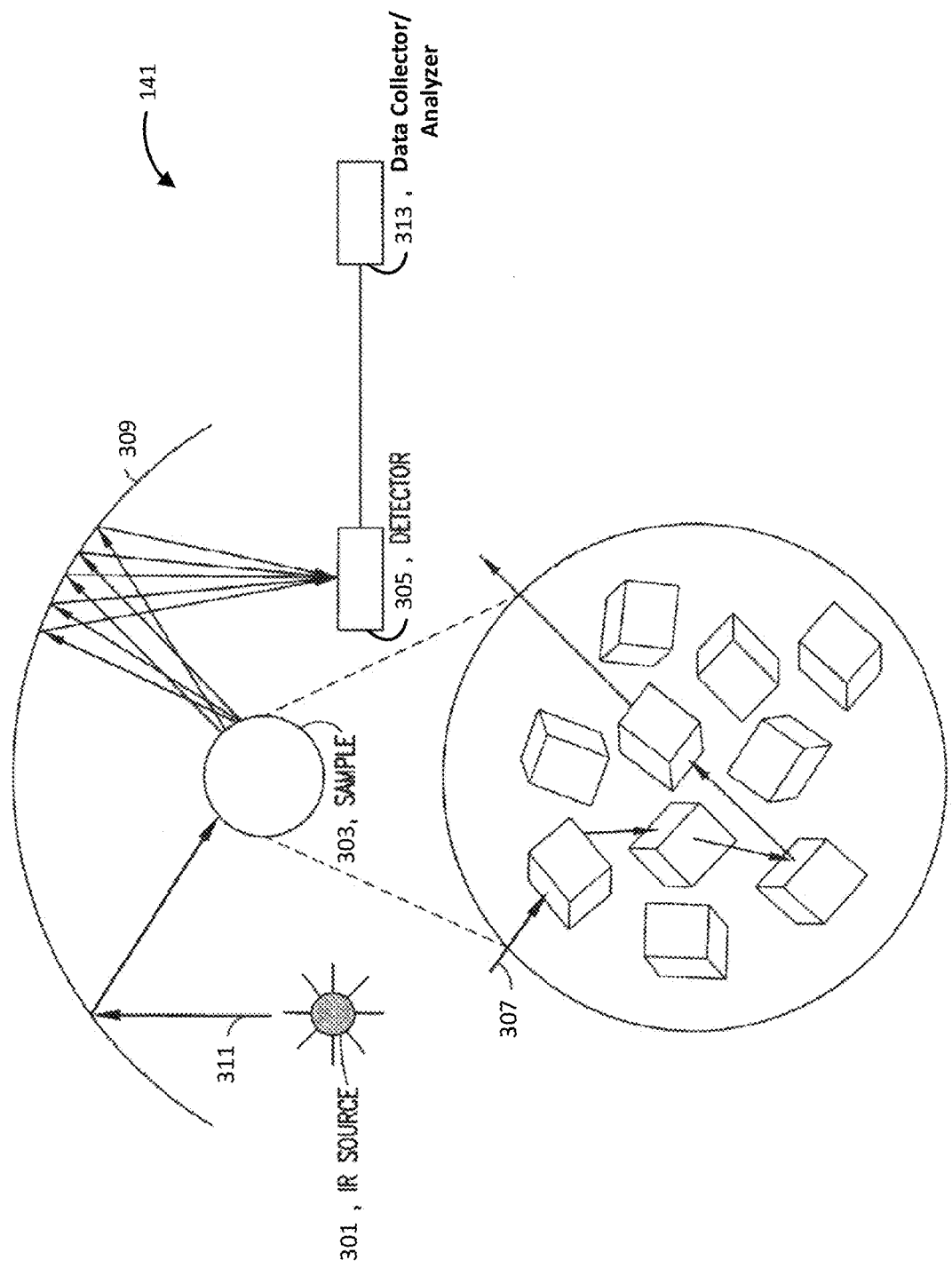
FIG. 4 is a schematic diagram of an exemplary spectrometer that performs diffuse reflectance infrared Fourier transform spectroscopy (DRIFTS) measurements, according to some embodiments.

FIG. 4 shows a schematic diagram of an exemplary spectrometer 141 that can be part of the analysis facility 150 and configured to conduct spectroscopy measurements on rock samples (e.g., cuttings). The spectrometer 141 employs the general mechanism of diffuse reflectance infrared Fourier transform spectroscopy (DRIFTS). DRIFTS responds to the modes of molecular vibrations of the components of the rock sample. In a non-limiting example, DRIFTS provides an easy and rapid measurement of cleaned cuttings, which can be analyzed to characterize the inorganic mineral components and kerogen of the cleaned cuttings. As depicted in FIG. 4, source 301 is a source of infrared radiation. Source 301 emits a beam of infrared radiation 311 that is directed to parabolic or spherical mirror 309, which in turn directs the beam to the rock sample 303 (e.g., cuttings). The incident infrared radiation 307 is specularly reflected, diffusely reflected, or transmitted through part of the sample 303. The reflected infrared radiation is captured by the parabolic or spherical mirror 309 and directed to the detector 305. The detector 305 collects and measures spectrum data that represents the diffusely reflected infrared radiation as output from the rock sample. The measured spectrum data represents the intensity of the diffusely reflected infrared radiation as output from the rock sample as a function of wavenumber (or wavelength). Each fundamental molecular vibration of the rock sample corresponds to a specific absorbance band in wavelength. The data collector/analyzer 313 performs a Fourier transformation on the measured spectrum data. The transformed spectrum data can be analyzed to quantity the mass fractions of mineral components of the rock sample (cleaned cuttings), the mass fraction of the kerogen in the rock sample (cleaned cuttings), and the matrix density of the rock sample (cleaned cuttings). Details of exemplary spectroscopy measurements and analysis that provide such data is set forth in co-owned U.S. patent application Ser. No. 13/447,109, entitled "Reservoir and completion quality assessment in unconventional (shale gas) wells without logs or core" and co-owned U.S. patent application Ser. No. 13/446,975, entitled "Method and apparatus for simultaneous estimation of quantitative mineralogy, kerogen content and maturity in gas shale and oil-bearing shale"; both filed on Apr. 13, 2012, the contents of which are herein incorporated by reference in their entireties.

For example, matrix density of the cuttings can be calculated as the sum of the mass fractions of the mineral components and organic-matter (kerogen) determined from the spectroscopy measurement divided by their known densities. For example, the matrix density calculation that accounts for both mineral components and kerogen in the solid matrix can be given as:

$$\frac{1}{\rho_{ma}} = \sum_i \frac{M_i}{\rho_{g_i}} + \frac{M_{ker}}{\rho_{ker}} \qquad \text{Eqn. (4)}$$

where $\rho_{ma}$ is the matrix density, $M_i$ is the mass fraction of the given mineral component i, $\rho_{gi}$ is the density of the given mineral component i, $M_{ker}$ is the mass fraction of kerogen, and $\rho_{ker}$ is the density of kerogen. The integral is performed over the mineral components of the cuttings.

Table 1 below provides known densities for kerogen, pyrite, and nine mineral components.

TABLE 1

The known densities of certain mineral components.
Kerogen density increases with thermal maturity.

| Phase | Density g/cm$^3$ |
| --- | --- |
| Quartz | 2.65 |
| Illite | 2.80 |
| Smectite | 2.78 |
| Kaolinite | 2.63 |
| Chlorite | 3.07 |
| Muscovite | 2.80 |
| Calcite | 2.71 |

TABLE 1-continued

The known densities of certain mineral components.
Kerogen density increases with thermal maturity.

| Phase | Density g/cm³ |
| --- | --- |
| Dolomite | 2.85 |
| Anhydrite | 2.97 |
| Pyrite | 5.01 |
| Kerogen | (1.0-2.0) |

Note that the most abundant sedimentary rock-forming minerals have relatively similar densities between 2.5 and 3.0 g/cm³, with a notable exception of pyrite with a density of 5.01 g/cm³. Note that pyrite is not measured directly by DRIFTS spectroscopy but is correlated to TOC using the ratio of organic carbon and sulfur from pyrite in anoxic marine sediments where C/S=2.8. The density of kerogen is related to its thermal maturity and falls within the range between 1 g/cm³ (waxy) and 2.0 g/cm³ (graphitic).

Figure 5:
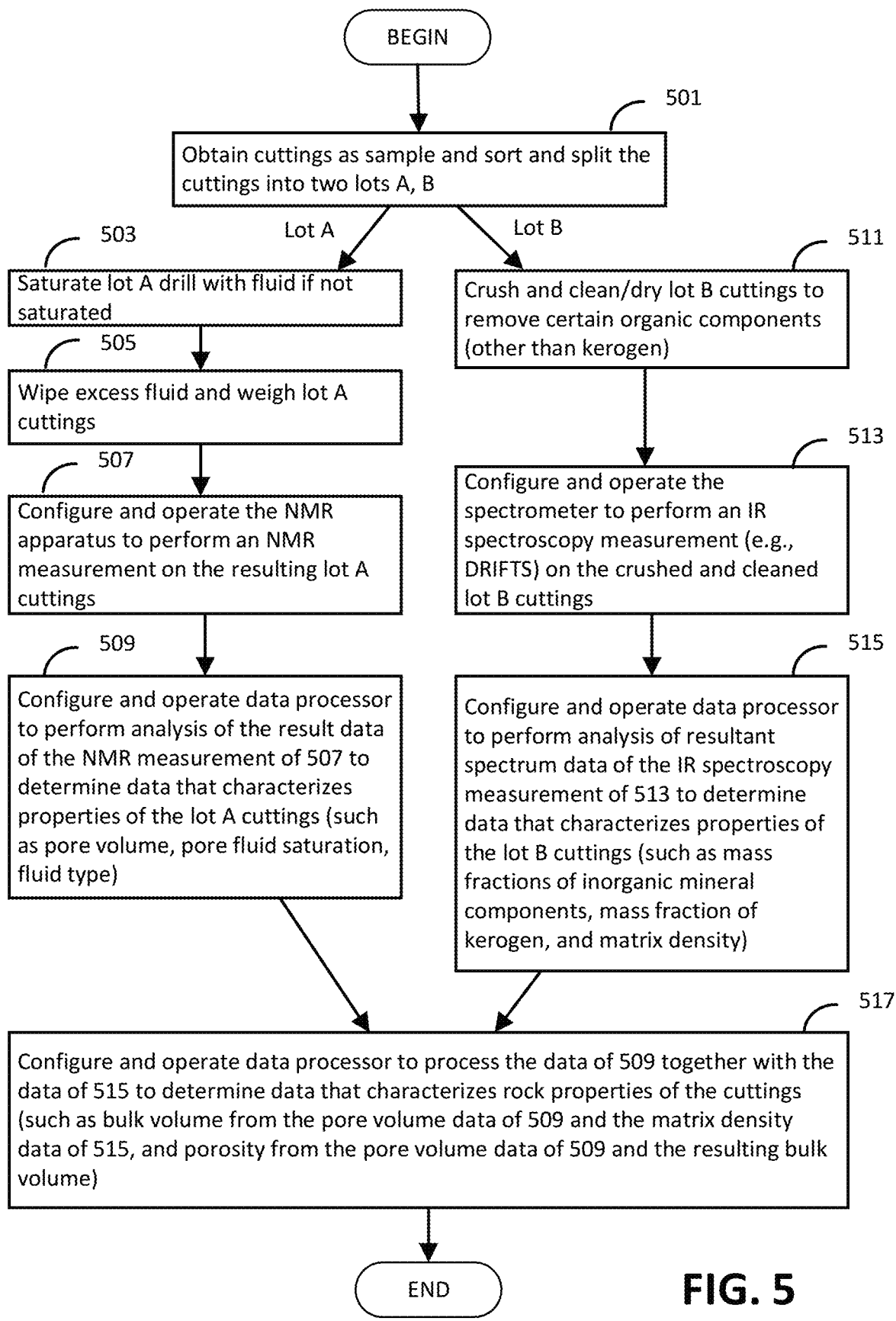
FIG. 5 is a flowchart that illustrates an exemplary workflow that combines an NMR measurement and an IR spectroscopy measurement to determine porosity of cuttings obtained from a subterranean formation, according to some embodiments.

FIG. 5 is a flowchart of an illustrative workflow that uses an NMR apparatus (for example, the NMR apparatus 140 of FIG. 2) and a spectrometer (for example, the DRIFT spectrometer 141 of FIG. 4) of the analysis facility to characterize rock properties of cuttings obtained from a formation (for example, cuttings obtained when drilling the formation 30 of FIG. 1).

In block 501, cuttings from the formation are collected (or otherwise obtained) and then sorted and split into two lots designated Lot A and lot B for the sake of description. The cuttings of Lot A can be selected by size such that they are appropriate for the NMR measurement as described in blocks 503 to 509 below. The cuttings of lot A are processed and subjected to the NMR measurement as described in blocks 503 to 509 below. The cuttings of Lot B are processed and subjected to a spectroscopy measurement as described in blocks 511 to 515 below. Result data obtained from the two measurements is combined and used to characterize rock properties of the formation in block 517 as described below.

In block 503, the cuttings of lot A are saturated with a fluid if not saturated already. The fluid can be a wetting fluid such as water or heavy water that is suitable for hydrogen proton NMR analysis. Importantly, the cuttings of Lot A are not cleaned or dried to remove soluble organic components from the cuttings as is done for the Lot B cuttings as described below.

In block 505, excess fluid can be wiped off the saturated cuttings of Lot A, and the resulting lot A cuttings can be weighed.

In block 507, the NMR apparatus (e.g., the NMR apparatus 140 of FIG. 2) is configured and operated to perform an NMR measurement on the resulting lot A cuttings. The NMR measurements can be carried out at the Larmor frequency of 2 MHz or possibly higher for measuring $^1$H nuclei. In block 509, a data processor (e.g., the data collector/analyzer 225 of FIG. 2) is configured and operated to perform analysis of the resulting data of the NMR measurement of 507 to determine data that characterizes properties of the lot A cuttings (such as pore volume, pore fluid saturation, fluid type). Details of exemplary NMR measurements and analysis that can be used to determine properties of the Lot A cuttings (such as pore volume, pore fluid saturation, fluid type) are described above.

In block 511, the cuttings of Lot B can be crushed (for example, into small size fragments that are approximately 50 microns in size or less) and cleaned and dried to remove certain organic components (other than kerogen) from the cuttings.

In block 513, the spectrometer (e.g., the spectrometer 141 of FIG. 4) is configured to perform a spectroscopy measurement (e.g., DRIFTS) on the crushed and cleaned lot B cuttings that result from 511. In block 515, a data processor (e.g., the data collector/analyzer 313 of FIG. 4) is configured and operated to perform analysis of the resultant spectrum data of the spectroscopy measurement of 513 to determine data that characterizes properties of the lot B cuttings (such as mass fractions of inorganic mineral components, mass fraction of kerogen, and matrix density). Details of exemplary spectroscopy measurements and analysis that can be used to determine properties of the Lot B cuttings (such as mass fractions of inorganic mineral components, mass fraction of kerogen, and matrix density) are described above.

In block 517, a data processor (such as CPU 144) is configured to process the data of 509 together with the data of 515 to determine data that characterizes rock properties of the cuttings.

For example, data representing the bulk volume ($V_{bulk}$) of the cuttings can be calculated from the pore volume data of 509 and the matrix density data of 515 as follows:

$$V_{bulk} = \left(\frac{(m_s - (V_{pore} * \rho_{fluid}))}{\rho_{ma}}\right) + V_{pore}, \qquad \text{Eqn. (5)}$$

where $m_s$ is the mass (in grams) of the lot A cuttings measured in 505, $V_{pore}$ is the fluid pore volume measured by NMR in 509, $\rho_{fluid}$ is the fluid density of the fluid that saturates the lot A cuttings, and $\rho_{ma}$ is the matrix density measured by spectroscopy in 515.

The liquid density $\rho_{fluid}$ can be based on liquid densities obtained from density measurements completed on separate fluid samples (associated with the same cuttings) using established techniques or based on model estimates for the liquid densities using composition and established density models from petroleum thermodynamics.

For example, the fluid that saturates the lot A cuttings can contain multiple components (or compounds) and the liquid density $\rho_{fluid}$ of such fluid may be calculated using a number of well-established methods by one skilled in the art, including mixing rules, density correlations, corresponding states, and equation of state (with or without volume translation). For example, the density of an ideal mixture of hydrocarbon compounds (i.e. no volume or enthalpy change upon mixing of the compounds) can be determined using a simple mixing rule:

$$\rho_{mix} = \sum \varphi_i \rho_i = \sum \frac{\rho_i}{w_i}, \qquad \text{Eqn. (6)}$$

where $\rho_i$ is the compound density, $\varphi_i$ is the volume fraction of compound i in the mixture and $w_i$ is the weight fraction of compound i in the mixture. However, most hydrocarbon mixtures are non-ideal, requiring the use of well-established density calculation methods that account for excess volume effects.

In another example, data representing porosity ($\varphi$) of the cuttings can be calculated from the pore volume data of 509 and the resulting bulk volume data as follows:

$$\varphi = V_{pore}/V_{bulk}, \qquad \text{Eqn. (7)}$$

where $V_{pore}$ is the fluid pore volume measured by NMR in 509, and $V_{bulk}$ is the bulk volume given by Eqn. (5).

The workflow determines porosity and other properties of the cuttings analyzed by both NMR and IR spectroscopy techniques. These properties are relevant to RQ and CQ. The cuttings can also be analyzed to estimate other quantities relevant to RQ and CQ, including thermal maturity, kerogen content, mineralogy, and surface area. Note that other IR spectroscopy or other forms of spectroscopy can be used in place of DRIFTS in this workflow for the property measurements, including but not limited to x-ray diffraction, x-ray fluorescence, and Raman spectroscopy, or a measurement of matrix density, such as with a pycnometer.

Cuttings Preparation

Figure 6:
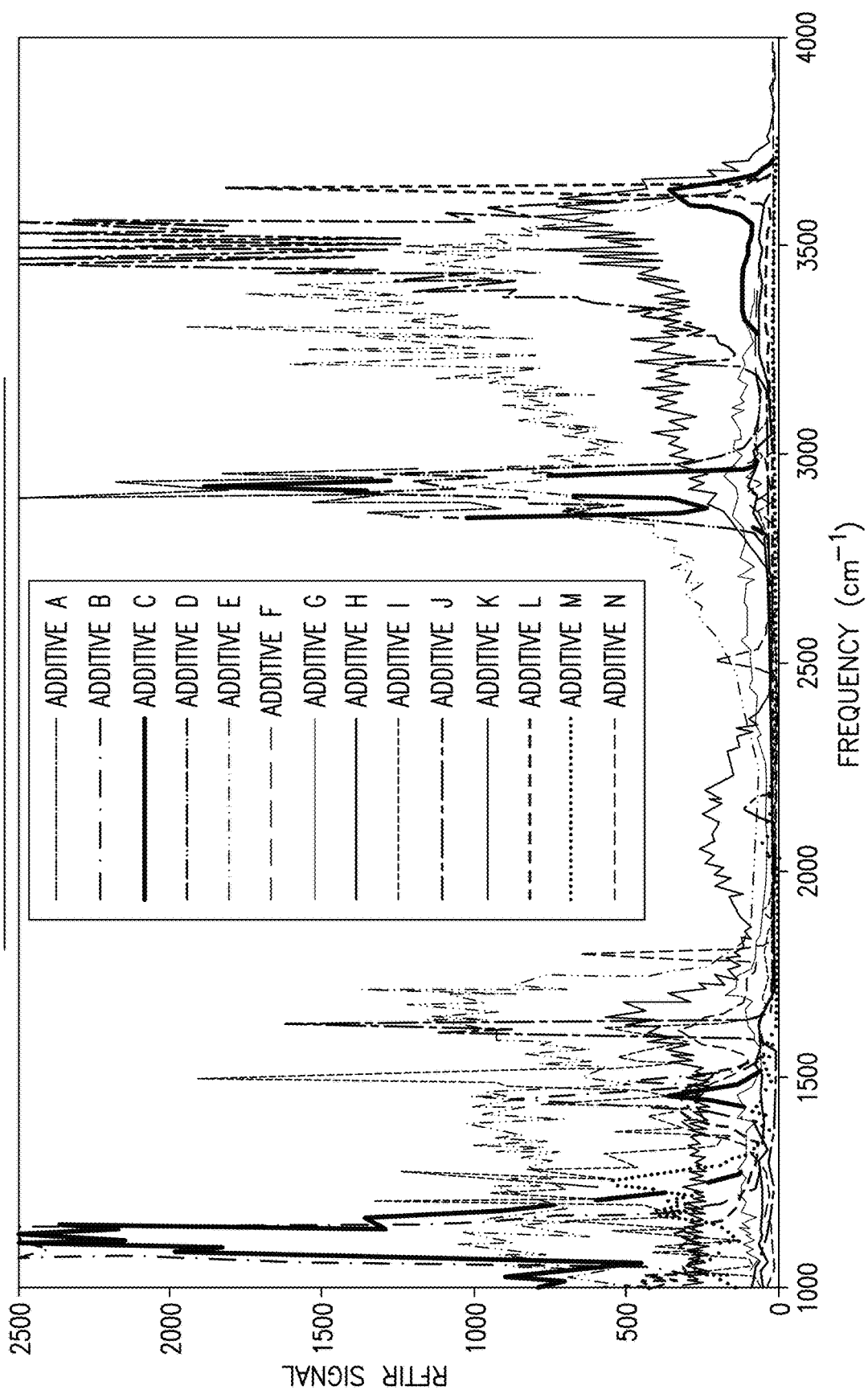
FIG. 6 is a plot of IR spectra for a number of solid and liquid drilling fluid additives measured by diffuse reflectance infrared Fourier transform spectroscopy.

Historically, limited information has been collected by FTIR or visual inspection of formation solids under a microscope, especially cuttings with residual drilling mud solvents. More involved analysis has not been selected because of the accuracy, time and cost for equipment and low likelihood of return of useful information. Moreover, the presence of drilling fluid in the cuttings can distort the FTIR analysis as shown in the plot of FIG. 6. Because of these issues, cuttings (such as the lot B cuttings in block 511) can be cleaned by any method to remove soluble hydrocarbons including solvent treatments or heat treatments prior to the FTIR analysis. Some exemplary embodiments are described below.

Historically preparation of cuttings samples often involves collecting material from a shale shaker, additional sorting via a small hand-held sieve, rinsing the material with the drilling fluid base oil, and then exposing the material to hexane. The hexane and other volatile organic material are baked out of the sample in an oven at 80° C. Soap and water may also be used to remove residual base oil.

Embodiments of the present disclosure can employ a cleaning procedure designed to prepare shale cuttings drilled with oil-based drilling fluid for spectroscopy analysis (for example by DRIFTS or other FTIR methods), gas sorption analysis as well as other measurements. With these specifications, the goals of the cleaning procedure are as follows:

1. Remove the base oil component of the drilling fluid from the cuttings. Initially, it is desirable to remove the cuttings from the drilling fluid, as is necessary for subsequent analysis of the cuttings. Cuttings can be removed from the drilling fluid using a shale shaker, which is a vibrating mesh with an opening around 150 microns. Cuttings are collected from the top of the shaker while drilling fluid falls through the shaker. The typical drilling fluid employs diesel fuel as a base oil. Diesel fuel contains large amounts of organic carbon and aliphatic hydrocarbon. Other drilling fluids can contain a synthetic oil as base oil. The synthetic oil also contains large amounts of organic carbon and aliphatic hydrocarbon. Some drilling fluids may use pentane, hexane, heptane, acetone, toluene, benzene, xylene, chloroform, dichloromethane, and a combination thereof. Detection of kerogen by FTIR involves detecting the amount of aliphatic hydrocarbon, so the base oil component of the drilling fluid that remains in the cuttings will be interpreted as kerogen. Detection of TOC by other techniques such as acidization, Rock Eval, and Fischer Assay involve detection of organic carbon, so the base oil component of the drilling fluid that remains in the cuttings will be interpreted as organic matter. The base oil component of the drilling fluid that remains in the pores of the cuttings will also prevent the gas in the gas sorption measurements from accessing those pores, reducing the measured surface area and pore volume.

2. Remove drilling fluid additives from the cuttings. Some drilling fluid additives contain large amounts of organic carbon and aliphatic hydrocarbon and thus will be interpreted as organic matter in the FTIR, acidization, Rock Eval, Fischer Assay and other measurements. Other drilling fluid additives will be interpreted as minerals that may be indigenous to shale, which will harm measurements of mineralogy such as FTIR, XRD, XRF, EDX, WDX, etc.

3. Do not alter the composition of the cuttings. The goal is to measure the properties of the cuttings in a manner that is representative of their state in the reservoir, so the cleaning process should not alter those properties. Most importantly, the cleaning procedure should not alter the mineralogy, kerogen content, thermal maturity, surface area, pore volume or porosity. An optional goal is to remove as little bitumen as possible. One of the goals of the mud logging is to estimate the kerogen content of the shale, so the preparation process should not destroy the kerogen. This is mostly straightforward because kerogen is insoluble in any solvent. Estimating the bitumen content is somewhat desirable; however, the bitumen content is typically an order of magnitude smaller than the kerogen content and estimation of the bitumen content is of secondary importance. Additionally, bitumen can be dissolved by drilling fluid, so in some cases the bitumen may be mostly removed by the time the cuttings reach the surface.

4. Reduce the cuttings particle size to around 10 microns. This particle size is required for many analyses, including FTIR and gas sorption. Briefly, large particles result in specular rather than diffuse reflection, complicating the interpretation of reflection FTIR measurements. With respect to gas sorption, the low permeability of shale necessitates small particle size to speed up the measurement.

Figure 7:
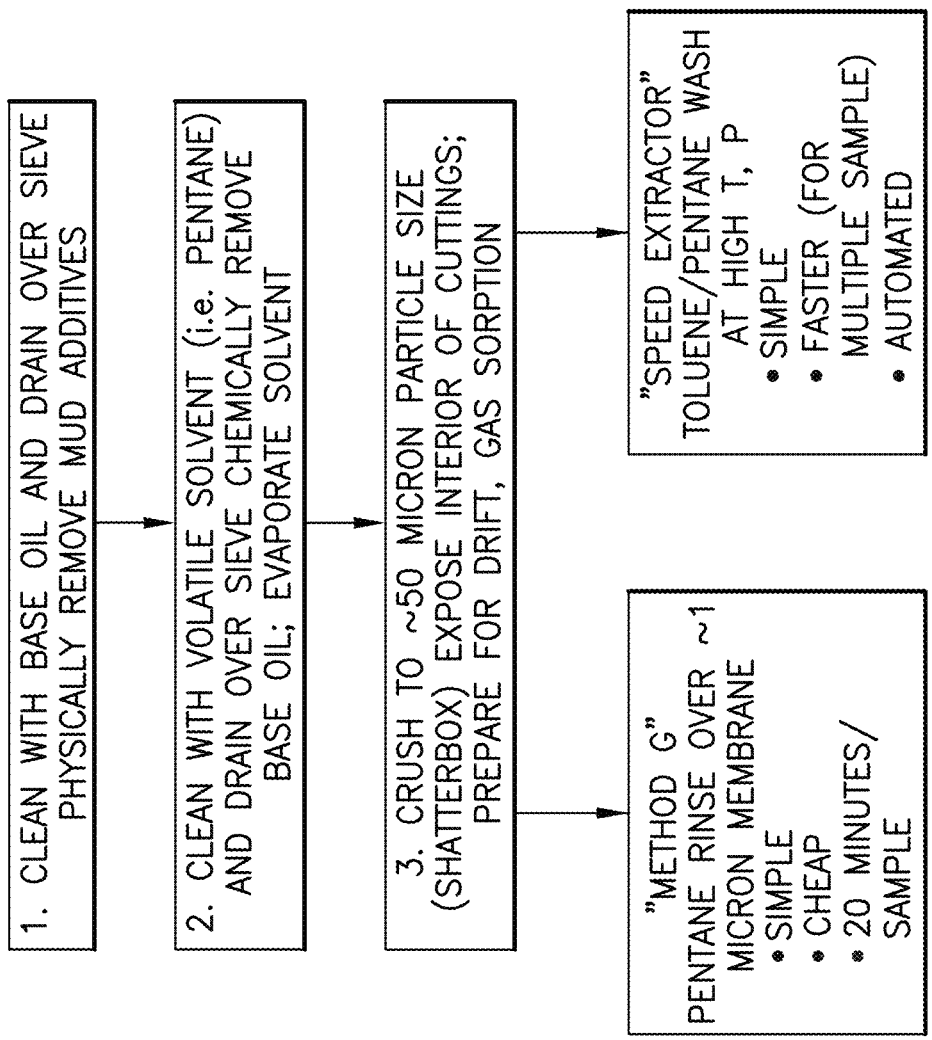
FIG. 7 is a flowchart that illustrates exemplary workflows for preparing cuttings for analysis, according to some embodiments.

A detailed cleaning procedure for preparing shale cuttings drilled with oil-based drilling fluid is set forth below. The procedure can be carried out at a wellsite or in the laboratory. FIG. 7 is a flow chart that illustrates the cleaning procedure, which is summarized below.

1. Collect cuttings from the shale shaker on a sieve. The sieve must have a mesh size about the same as that of the shale shaker.

2. Rinse the cuttings with the base oil of the drilling fluid. The base oil of some embodiments may include diesel, mineral oil, paraffin oil, and synthetic oils such as ester and olefin oils. This step removes residual drilling fluid additives mixed with and loosely attached to the cuttings. Large quantities of base oil are typically readily available on the rig floor for this purpose. The rinsing should last for a couple of minutes. For example, one might rinse the cuttings over the sieve until the rinsate appears free of particulate contamination. FIG. 7 includes a step labeled "1" that describes cleaning the cuttings with a base oil and draining the cuttings over a sieve to physically remove drilling fluid additives from the cuttings. For this step and step 3 below, the sieve may be a hand-held device that is not automated. For some embodiments, the sieve may be an automated shaking instrument, such as a rock tumbler. Further, a surfactant may be selected for both steps. The surfactant may include ethylene glycol monobutyl ether or a similar surfactant.

3. On the same sieve, rinse the cuttings with a solvent such as pentane. The purpose of this step is to remove enough of the base oil from the surface of the cuttings so that the cuttings can be crushed (see the following step; wet cuttings form a mud during crushing and do not crush well). The rinsing should last for a couple of minutes. Pentane is ideal for this step for two reasons. First, pentane is volatile, meaning that it will evaporate quickly after being used to clean the cuttings. Hence, without requiring an additional step, pentane evaporates, resulting in a sample that is sufficiently dry for crushing. Second, pentane dissolves diesel, but it does not dissolve kerogen and may not dissolve all bitumen. Bitumen is a complex mixture of compounds with a wide range of solubilities, and selection of a solvent that dissolves diesel but does not dissolve any fraction of bitumen is impossible. However, bitumen is dominated by resins and asphaltenes, neither of which are dissolved by pentane, meaning that pentane dissolves only some fraction of bitumen. Other common laboratory solvents that will suffice for this application include hexane, heptane, acetone, toluene, benzene, xylene, chloroform, dichloromethane, etc. FIG. 7 includes a step labeled "2" that describes cleaning the cuttings with a volatile solvent such as pentane and draining the cuttings over a sieve. This is to chemically remove the base oil and evaporate the solvent.

4. Crush the cuttings to a particle size of around 10-40 microns. This is the optimum size for gas sorption (small enough to allow measurement in reasonable time but not so small as to create additional surface area) and for FTIR (small enough to minimize specular reflection and to minimize scattering in transmission mode). The crushing should be accomplished with an automated instrument such as a SHATTERBOX™ (commercially available from SPEX SamplePrep of Metuchen, NJ). The crushing could be accomplished with a mortar and pestle, but the reproducibility of this processing is not comparable to automated techniques. This crushing could also be accomplished with a mixer mill such as Mixer Mill MM 400 which is commercially available from Retsch of Newton, PA. FIG. 7 includes a step labeled "3" that describes crushing the particles to approximately 50 microns or less to expose the interior of the cuttings and prepare for DRIFT spectroscopy or gas sorption analysis. Some embodiments may use any method to reduce the size of the sample such as crushing, grinding, shaking or a combination thereof.

5. Rinse the cuttings again with a solvent. The initial rinsing steps are unlikely to remove all of the drilling fluid that invaded the cuttings while the cuttings were in the wellbore. For example, in many cases, the drilling fluid can invade the cuttings for 1-3 hours (which is the average time required for the cuttings to reach the surface) and do so at elevated temperature (resulting in low viscosity) and elevated pressure (resulting in enhanced saturation). Such invasion is far different from the initial rinses, which last only a few minutes and occur at ambient temperature and pressure. It is likely that the effect of temperature and pressure support a more thorough invasion of drilling fluid than solvent achieves under ambient conditions. After crushing, the characteristic length of the particles is reduced by orders of magnitude, which promotes a more efficient cleaning. So, the purpose of this step is to clean the cuttings more efficiently than can be performed with the steps 1-3 above. Below are two possible techniques for accomplishing this step 5.

One option for step 5 is to clean the cuttings over a vacuum filter. A vacuum filter is a standard piece of equipment in a chemistry laboratory. It involves a fritted piece of glassware, with a filter membrane resting on it. Because the cuttings have been crushed to 10 microns, a filter membrane with a smaller pore size is required (sieves are not an option here because sieves with openings below 10 microns are not available). An example filter membrane that is readily available is a 0.45-micron polycarbonate filter membrane. Below the frit is a volume evacuated by a pump. The cuttings are placed on top of the filter membrane at atmospheric pressure, solvent is added and the vacuum on the other side of the frit forces the solvent to flow through the cuttings. This process efficiently removes residual drilling fluid from the cuttings because of the small particle size. Pentane is the optimum choice of solvent for the same reasons as above. Alternative solvents listed above may be selected for this step. FIG. 7 lists a step labeled "Method G" which uses a pentane rinse over a 1-micron membrane which is simple, cheap, and takes approximately 20 minutes per sample.

Another option for step 5 is to clean the cuttings at elevated temperature and pressure. Cleaning at elevated temperature and pressure can be achieved in an instrument such as the SPEED EXTRACTOR™ manufactured by Buchi of Newcastle, DE, which lowers the viscosity, allowing the solvent to invade the particles quickly: high temperature also increases the solvating power, allowing the diesel to be dissolved more easily: high pressure forces the solvent into the cuttings more quickly: high pressure also allows the temperature to be increased beyond the atmospheric-pressure boiling point without vaporizing, allowing further increases in temperature. Combined with the small particle size, this technique cleans the cuttings quickly and effectively. However, this technique is more likely to remove bitumen. If removing bitumen from the cuttings is a goal, this step could be performed with powerful solvents such as toluene that will remove bitumen from the cuttings even more effectively. Example operating conditions include using toluene as a solvent, at 150° C. temperature and 50 bar pressure for approximately 30 minutes. This technique can be handled in an automated way, requiring only a few minutes of operator time. Taking advantage of the automation, a quick final rinse with a volatile solvent such as pentane can be applied after the toluene rinse to accelerate evaporation. Another advantage of this technique is that these conditions can dissolve drilling fluid additives that are not dissolved in room temperature solvent (save for very long exposure times) thereby removing mud additives beyond those loosely attached to the cuttings. This technique can also be performed on multiple samples at once. FIG. 7 includes a step labeled "Speed Extractor" which uses a toluene and/or pentane wash at temperatures or pressures higher than the sample temperature which is simple, faster for multiple samples, and automated.

Some embodiments may benefit from exposing the sample to a second cleaning fluid and using vacuum filtration and/or solvent extraction. In some embodiments, the extraction occurs at higher temperature and/or higher pressure than the sample temperature and pressure. Some embodiments may have a final rinse with a volatile solvent.

After completing these steps, the cuttings are sufficiently clean, have the correct particle size, and have retained their kerogen. They are now ready for analysis of thermal maturity, organic content, mineralogy, surface area, pore volume, porosity, etc. by instruments such as IR spectroscopy, gas sorption, among many others. Additional tests may include TOC analysis by acidization, Rock Eval, Fischer Assay, XRD, XRF, WDX, EDX, gas sorption, pycnometry, and porosimetry.

Results

For the purpose of quality assurance, four well-characterized conventional quarry rock samples (two limestone, a dolomite, and a sandstone) and four oil shale samples (instead of actual drilling cuttings samples) were used in a study. For each rock sample, a regularly shaped plug (20×7 mm) was drilled and trimmed to fit the NMR probe dimensions. Simulated cuttings were obtained by breaking the sample into gravel-sized pieces with a mortar and pestle and then sieving to obtain fragments with a particle size between 1 and 5 mm. The conventional rock samples were pressure saturated to 1200 psi with brine and the shale samples were pressure saturated to 2000 psi with dodecane. Samples were stored in their saturating fluid until they needed to be measured. A representative split (5 g) of the unsaturated, cuttings-sized pieces was retained for a DRIFTS spectroscopy measurement.

Prior to the NMR measurement, the core and cuttings samples were wiped of outer fluid with printer paper and weighed. Because the NMR measurements are sensitive to all the $^1H$ nuclei, any fluid that is not in pores could lead to an inaccurate estimation of pore fluid volume, therefore it is important to remove the outside fluid without losing the fluid in the pores. The saturated samples were measured using a 12 MHz Niumag permanent magnet benchtop NMR fitted with a 10-mm RF probe. The $T_2$ relaxation times of the saturated rocks were measured using a Carr-Purcell-Meiboom-Gill (CPMG) pulse sequence. The echo spacing used was 200 microseconds, the number of echoes was 1000, and the recycle delay was set to 2 seconds. The total acquisition time plus processing took 10 minutes per sample. Probe dimensions and coil length were considered when preparing the samples. For an accurate measurement of the pore fluid volume, the samples needed to be centered within the probe and large enough to fill the sensitive area of the RF coil, but also well below the upper limit of the coil dimensions. Due to these restrictions, samples, both core and cuttings amounts, were kept to 20 mm in length. NMR measurements have been shown to be able to not only determine the total fluid volumes but also their types (bitumen versus water versus oil) and the environments they occupy (clay associated water versus bulk water, oil in organic versus inorganic pores).

The cuttings were prepared for the DRIFTS spectroscopy measurement by crushing the split of dry cuttings samples to a fine powder in a swing mill. The shale samples were cleaned with n-pentane to remove soluble hydrocarbons and then dried. A DRIFTS infrared spectroscopy measurement was made using a Bruker Alpha-R spectrometer. The spectrometer measures the intensity of diffusely reflected IR radiation returned to the spectrometer after interacting with the cleaned cuttings. The spectral measurement is made over the mid-IR region between wavenumbers 400 and 4000 $cm^{-1}$. The intensity of diffusely reflected light at each frequency in the measured spectrum is a function of the abundance of chemical bonds in the sample (i.e., chemical bonds in inorganic minerals and organic compounds), which vibrate and absorb IR radiation at characteristic frequencies. The reflected IR spectra is given in Kubelka-Munk (KM) units. The resulting KM spectrum is uniquely described by the type and abundance of molecular vibrations in the sample and so is a direct function of the mineral and organic matter concentrations.

Figure 8:
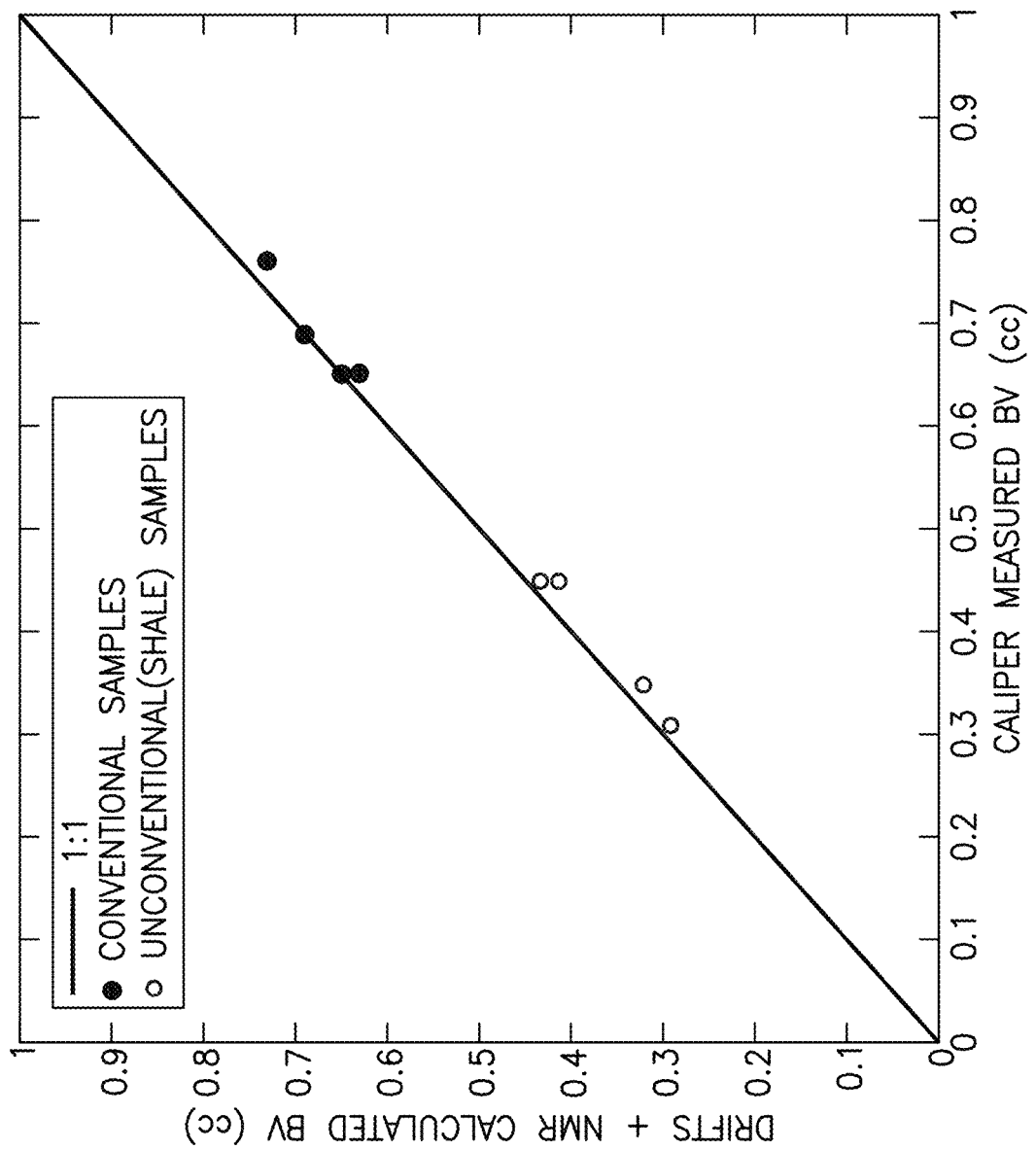
FIG. 8 is a plot of the bulk volume of the core plug samples measured using a caliper (x-axis) versus the bulk volume of the corresponding cuttings obtained using NMR measured pore volume, DRIFTS measured matrix density and the sample weight (y-axis).

FIG. 8 is a plot of the bulk volume of the plug samples measured using a caliper (x-axis) versus the bulk volume of the corresponding cuttings obtained using NMR measured pore volume, DRIFTS measured matrix density and the sample weight (y-axis). The caliper measured bulk volume compares well with the NMR-DRIFTS bulk volume to within 0.01 cc on average and shows the successful application of this method for these regularly shaped core samples. The black markers correspond to the conventional rock samples and the grey markers represent the unconventional rock (shale) samples.

Figure 9:
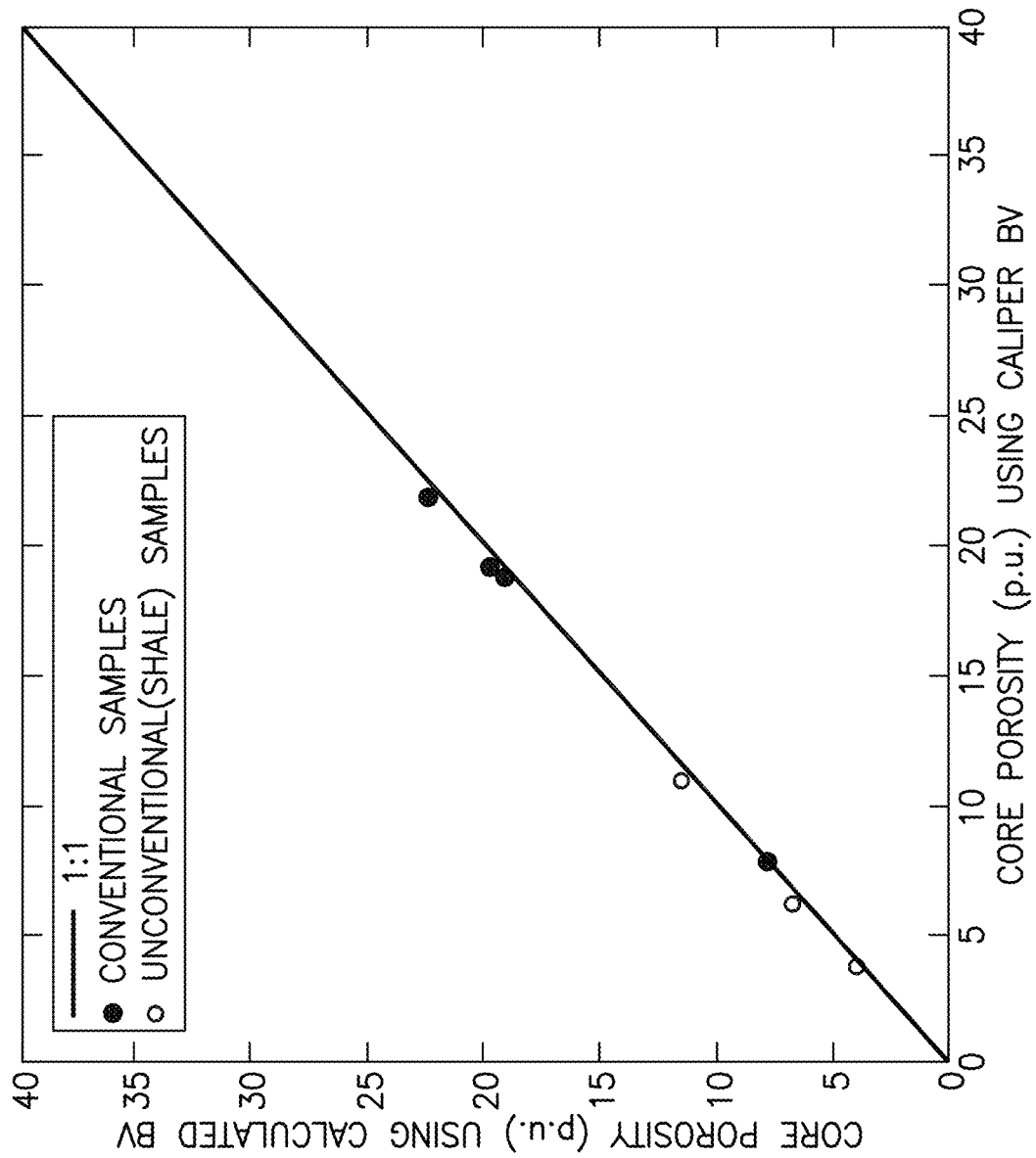
FIG. 9 is a plot of porosity of the core plug samples measured using NMR pore volumes and caliper measured bulk volume (x-axis) as compared to porosity of the plug samples using NMR pore volumes and DRIFTS calculated bulk volume (y-axis).

FIG. 9 is a plot of porosity of the plug samples measured using NMR pore volumes and caliper measured bulk volume (x-axis) as compared to porosity of the plug samples using NMR pore volumes and DRIFTS calculated bulk volume (y-axis). The agreement is very good, within less than 1 p.u. on average, which shows that combining DRIFTS and NMR can provide a good estimate of the porosity for regularly shaped saturated samples. Additional measurements on samples from several basins can possibly provide better quantification of the error bars for this measurement and the factors upon which it depends.

Figure 10:
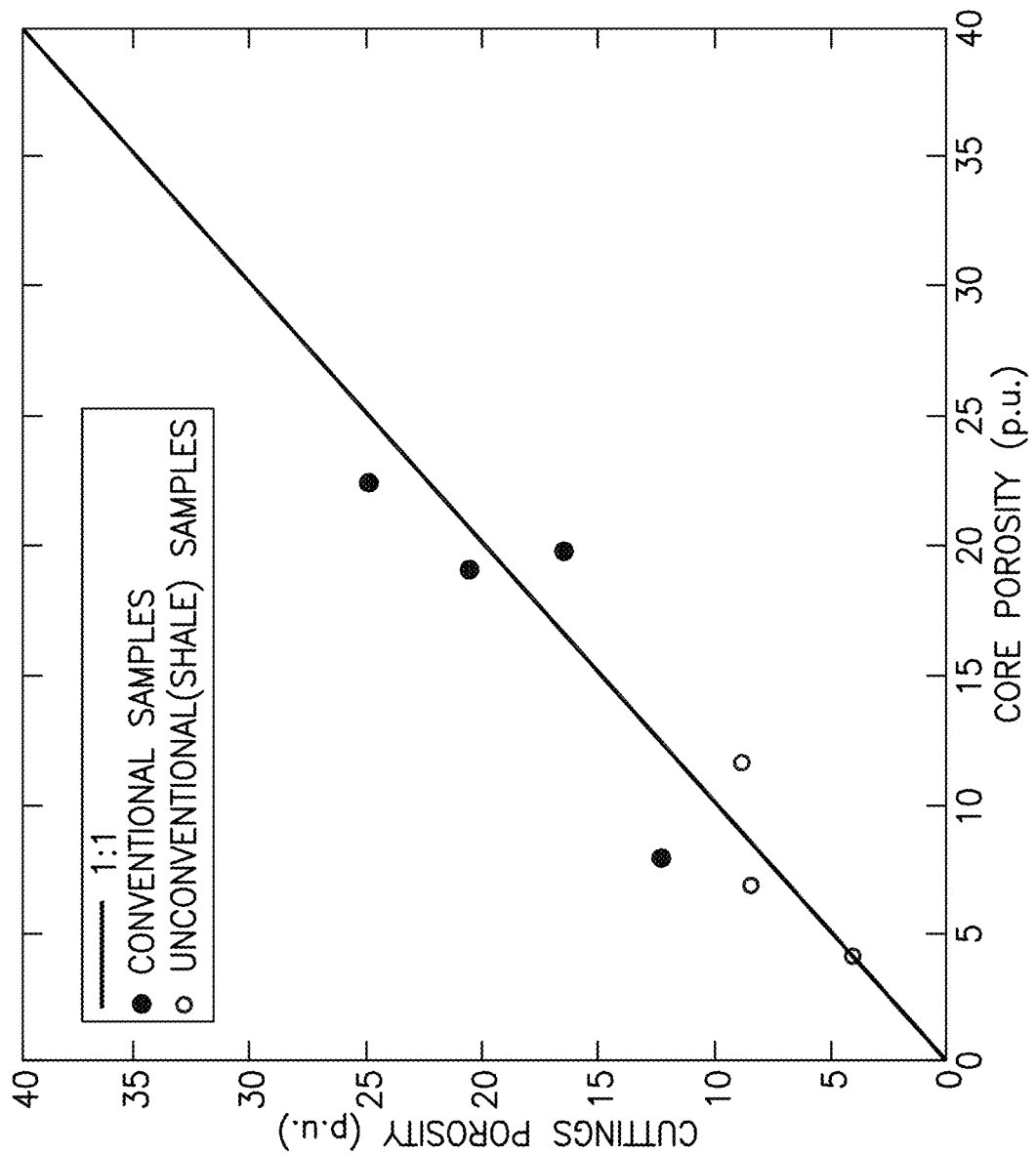
FIG. 10 is a plot of the porosity of the plug sample (x-axis) as compared to the porosity of the cuttings (y-axis) where both are calculated using the calculated bulk volume from combined DRIFTS and NMR measurements.

Since a benchmark for measuring the bulk volume of the cutting samples is not provided, FIG. 10 provides a plot of the porosity of the plug sample (x-axis) vs. the porosity of the cuttings (y-axis) where both are calculated using the calculated bulk volume from DRIFTS and NMR. Agreement between the plugs and cuttings are reasonable. Heterogeneity between splits of the whole rock (the measured cuttings were not made from the measured core) could contribute to the small scatter observed in the data.

The results presented show that pore volume calculated from NMR and bulk volume from DRIFTS matrix density measurements on saturated samples is a quick and effective way to measure porosity of regularly-shaped saturated core samples and irregularly-shaped saturated cuttings samples in the absence of log data. By combining NMR and DRIFTS measurements, and from the cuttings alone, we can obtain information on the reservoir's mineralogy and porosity allowing for a more conclusive assessment of reservoir quality. The NMR measurements average about a few minutes in duration with an additional couple of minutes for the sample cleaning. If the saturation of the shale cuttings is necessary, that would take additional time and needs to be determined. DRIFTS measurement including sample collection and thermal cleaning is about 25 minutes in duration. The cleaning and measurements for both NMR and DRIFTS measurements can also be automated if desired.

In order to prepare cuttings for the NMR measurements described herein, the cuttings can be subject to sieving between greater than 1 mm and less than 5 mm. The sieving above 1 mm can help avoid mud additives and improve the NMR signal. The sieving less than 5 mm can help avoid cavings. After separating the cuttings, the mud and fluid can be removed from the outside of the cuttings (e.g. by wiping with paper) and the sample weighed. The sample preparation for the DRIFTS measurement would remain unchanged. It is understood that cuttings may have lost some of the original pore fluid as they travel to the surface for collection and that the cuttings may be fractured, perturbing the calculated porosity. However, in such cases the relative changes in porosity or the quantities of pore fluids (such as bitumen, oil in organic pores, oil in inorganic pores etc.) based on cuttings analysis may indicate important changes in reservoir conditions even when quantitative information may not otherwise be available.

Figure 11A:
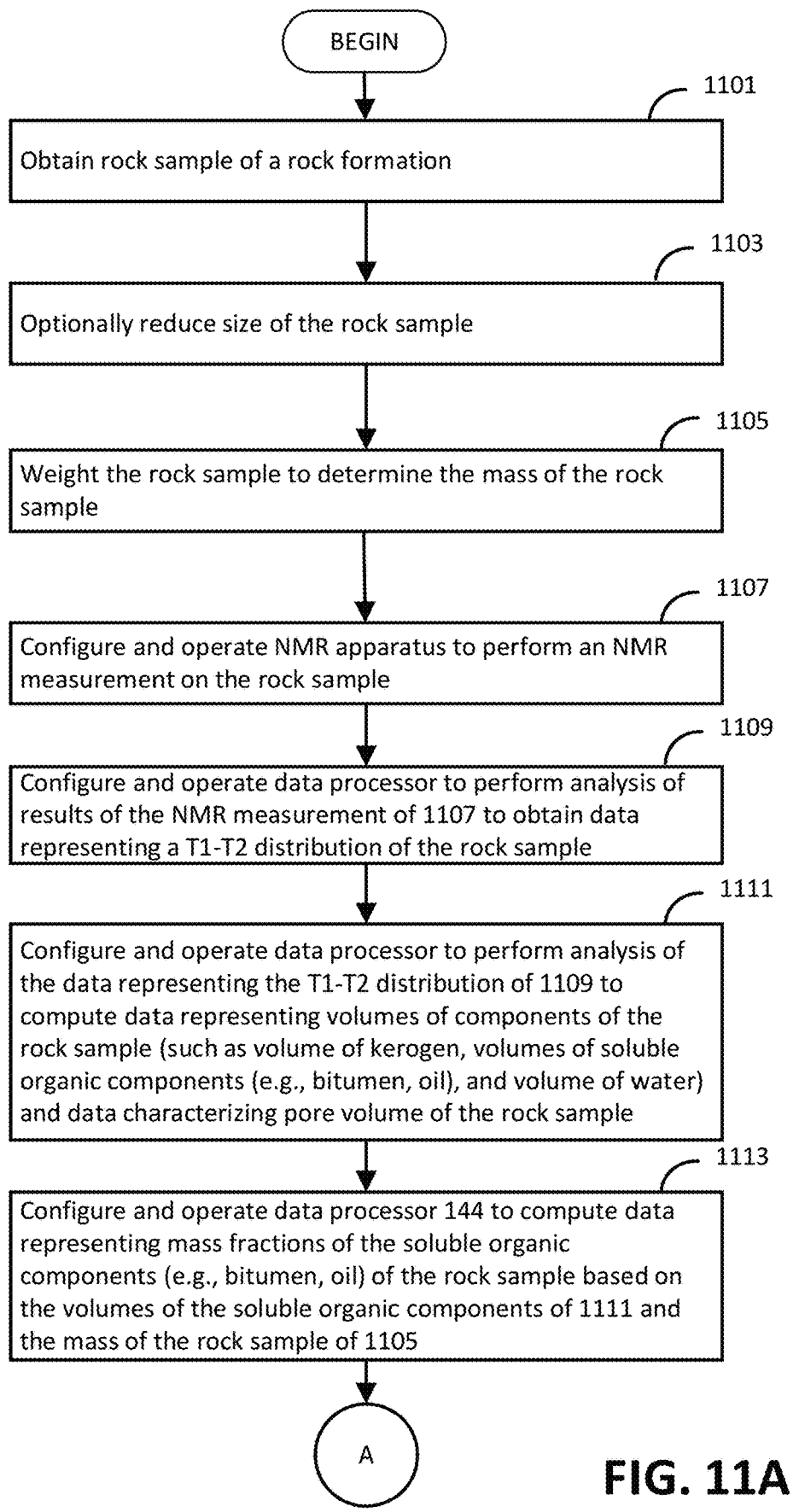
FIGS. 11A-11C, collectively, is a flowchart that illustrates an exemplary workflow that combines NMR measurements and IR spectroscopy measurements on an unprepared rock sample (without cleaning with a solvent) to determine properties of kerogen in the rock sample.
Figure 11B:
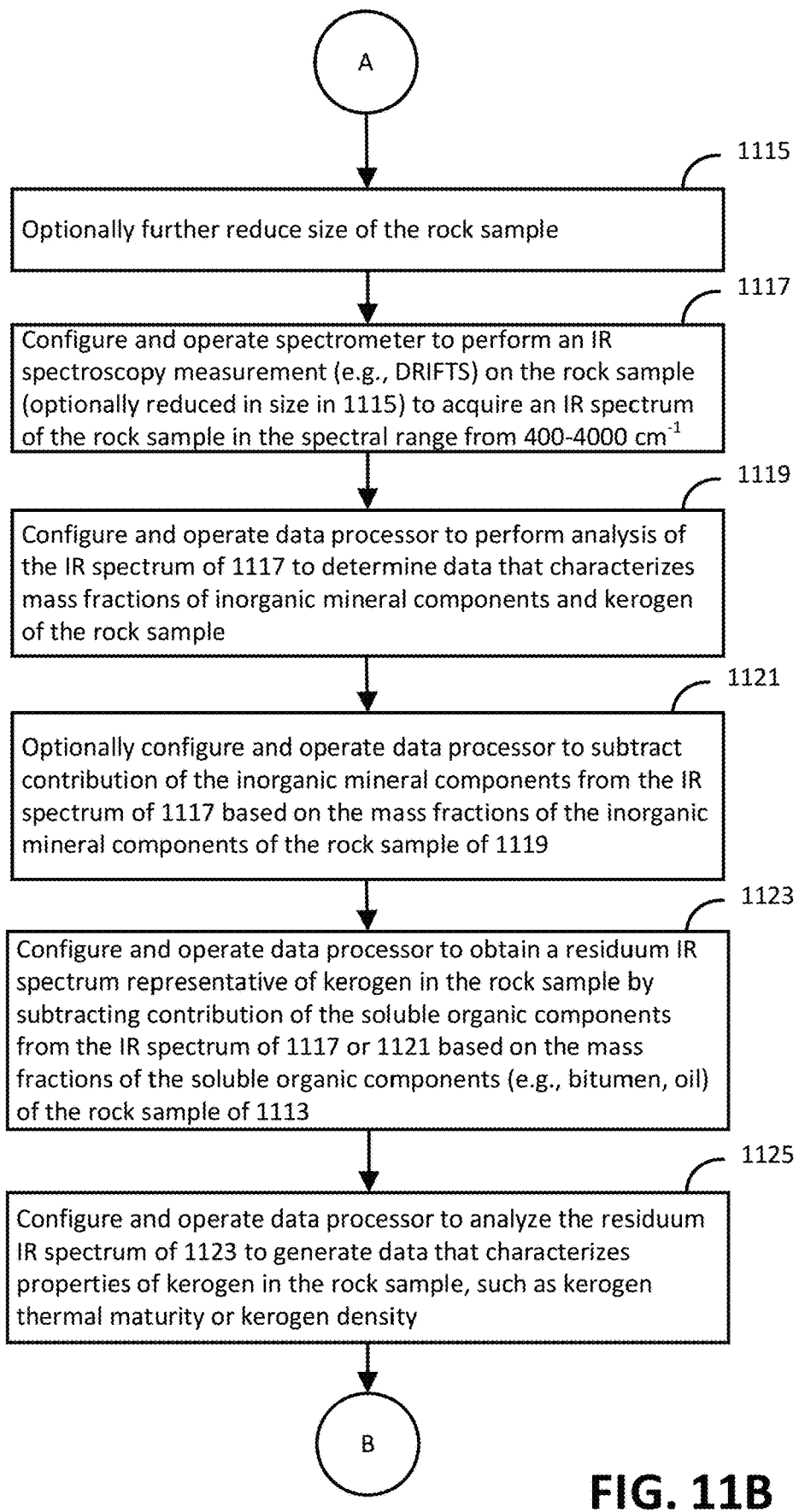
Figure 11C:
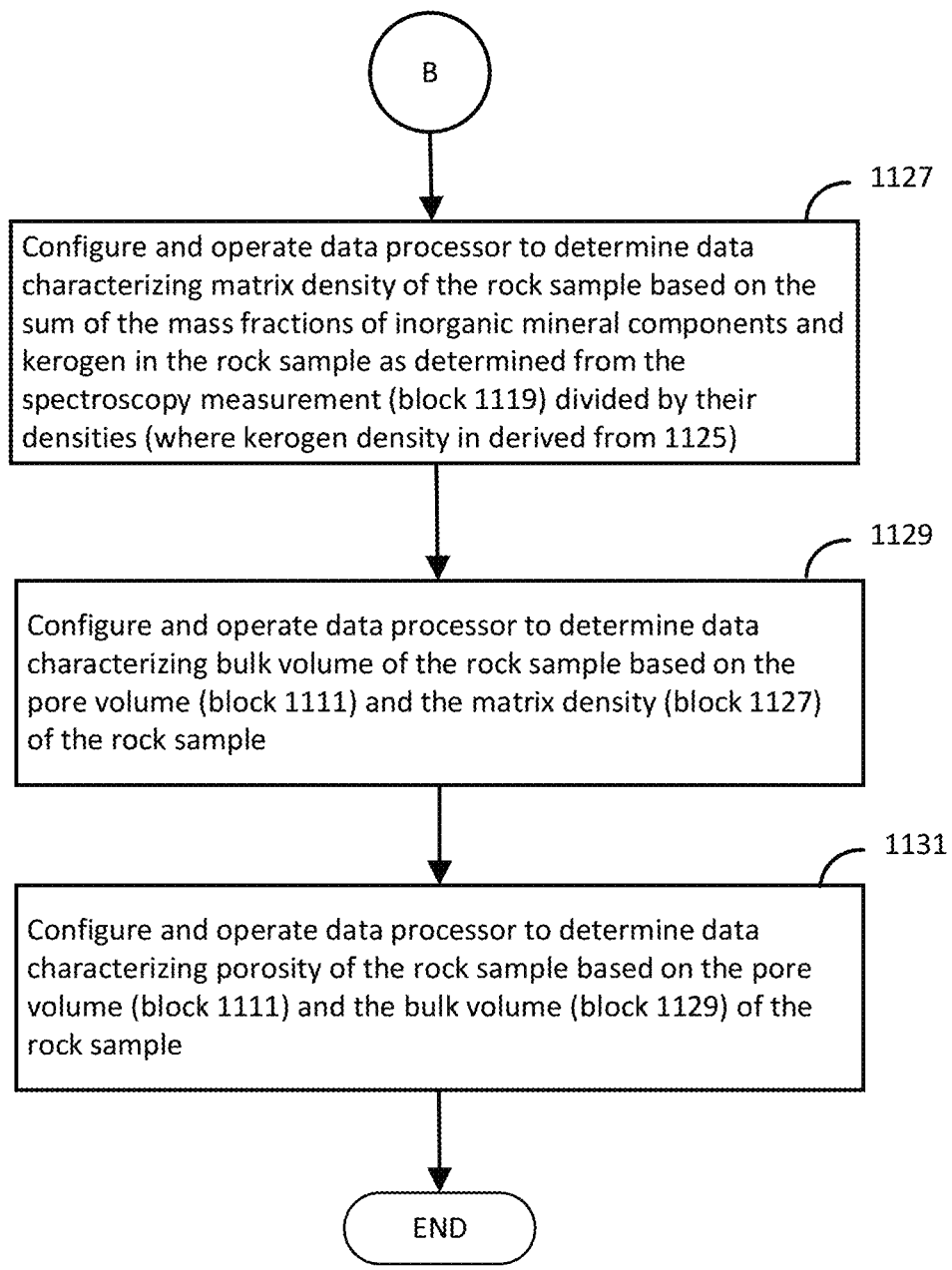

Embodiment Employing Combined NMR-Spectroscopy Measurements without Efficiently Cleaning Rock Samples In an alternate embodiment, a workflow is provided that combines NMR and IR spectroscopy measurements without the need for efficiently cleaning rock samples. For a native formation sample comprising both matrix (comprising one or more of at least minerals and kerogen) and pore volumes (comprising one or more of at least bitumen, oil, and water), the NMR measurement provides the determination of fluid-filled pore volumes, and the IR spectroscopy measurement provides the determination of matrix volumes which may be complicated by the presence of pore-fluid components (e.g., bitumen, oil) whose spectral response is identical or nearly identical to that of matrix components (i.e., kerogen). The NMR measurement on the same formation sample provides the minimum determination of soluble organic (non-kerogen) components within the pore volume such that their contribution to the measured IR spectrum can be 'corrected' from the contribution of kerogen within the matrix. Such a workflow is shown in the flowchart of FIGS. 11A-11C and described below.

In block 1101, a sample of a rock formation is collected or otherwise obtained. The sample may be cuttings, a core plug, or other rock sample type or form. When collected as a function of depth, the prescribed workflow will provide a 'log' of desired property values (e.g., thermal maturity) as a function of depth.

In block 1103, optionally, the size of the rock sample can be reduced to a size relevant for the NMR measurement (block 1107). Such a method might comprise, for example, reducing inch-size or larger core plugs to centimeter-size chips to fit within the sample holder for the NMR measurement.

In block 1105, the rock sample (which has been optionally reduced in size in 1103) is weighed to determine the absolute mass $M_R$ of the rock sample. In the given notation for $M_R$, the subscript R refers to the rock formation, comprising matrix (e.g., minerals, kerogen) and fluid (e.g., bitumen, oil, water).

In block 1107, an NMR apparatus (such as the NMR apparatus 140 of FIG. 2) is configured and operated to perform an NMR measurement on the rock sample weighed in 1105. The NMR measurements can be carried out at the Larmor frequency of about 5 MHz to 50 MHz for measuring $^1$H nuclei. The NMR measurement of block 1107 can be done in the field (e.g., wellsite) or in a laboratory. Frequencies higher than 50 MHz can also be suitable for laboratory purposes.

In block 1109, a data processor (such as the data collector/analyzer 225 of FIG. 2) is configured and operated to perform analysis of the result data of the NMR measurement of 1107 to acquire $T_1$-$T_2$ distribution of the rock sample. Such computations can employ NMR interpretations well-known to those skilled in the art as described herein.

In block 1111, a data processor (such as the data collector/analyzer 225 of FIG. 2 or the CPU 144 of FIG. 1) can be configured and operated to perform analysis of the data representing the $T_1$-$T_2$ distribution of 1109 to compute data representing volumes of components of the rock sample (such as volume of kerogen, volumes of soluble organic components (bitumen, oil), and volume of water) and data representing pore volume of the sample. Such computations can employ NMR interpretations well-known to those skilled in the art. The absolute volume for a given component of the rock sample is here given notation Vi where subscript i refers to kerogen $V_K$, bitumen $V_B$, oil $V_O$, etc. The pore volume of the sample can be determined by adding together the volumes for the different fluid components.

In block 1113, a data processor (such as the data collector/analyzer 225 of FIG. 2 or the CPU 144 of FIG. 1) can be configured and operated to compute data representing mass fractions of the soluble organic components of the rock sample based on the volumes of the soluble organic components of 1111 and the mass of the rock sample of 1105. For example, the mass fraction of bitumen $m_B$ in the rock sample can be computed from the relationship:

$$m_B = [V_B \cdot \rho_B]/M_R, \quad \text{Eqn. (8)}$$

where $\rho_B$ is the absolute mass density of bitumen, $V_B$ is the volume of bitumen in the rock sample as determined in 1111; and $M_R$ is the absolute mass of the rock sample as determined in 1105.

In another example, the mass fraction of oil $m_O$ in the rock sample can be computed from the relationship:

$$m_O = [V_O \cdot \rho_O]/M_R, \quad \text{Eqn. (9)}$$

where $\rho_O$ is the absolute mass density of oil, $V_O$ is the volume of oil in the rock sample as determined in 1111; and $M_R$ is the absolute mass of the rock sample as determined in 1105.

In block 1115, optionally, the rock sample (which was weighed in 1105 and possibly subject to the NMR measurement in 1107) can be reduced in size to a size relevant for the IR measurement (block 1117).

In block 1117, a spectrometer (such as the spectrometer 141 of FIG. 4) is configured and operated to perform an IR spectroscopy measurement (e.g., DRIFTS) on the rock sample (which was weighed in 1105 optionally reduced in size in 1115) to acquire an IR spectrum of the rock sample in the spectral range from 400-4000 cm$^{-1}$. The IR spectroscopy measurement can be done in the field (e.g., wellsite) or in a laboratory. The IR spectroscopy measurement can be done using any mode of IR spectroscopy, such as transmission, diffuse reflectance, attenuated total reflectance, etc., but is here exemplified using diffuse reflectance techniques (DRIFTS). FIG. 12A-12E illustrate the DRIFT spectra of a formation sample comprising several discrete and identifiable components, including minerals such as quartz (characteristic vibration modes between approximately 1200 and 1400 cm$^{-1}$) and kaolinite (characteristic vibration modes between approximately 3600 and 3750 cm$^{-1}$), and organic matter such as bitumen and kerogen (characteristic vibration modes between approximately 1400 and 750 cm$^{-1}$ and between approximately 2800 and 3100 cm$^{-1}$).

In block 1119, a data processor (such as the data collector/analyzer 313 of FIG. 4) is configured and operated to perform analysis of the IR spectrum of 1117 to determine data that characterizes mass fractions (mass concentrations) of inorganic mineral components and kerogen of the rock sample. In embodiments, the mass fractions of the inorganic mineral components and kerogen in the sample(s) can be determined from the measured IR spectrum using methods such as a least squares regression well-known to those skilled in the art. The mass fractions of the inorganic mineral components and kerogen and their sum can be referred to by a notation $m_j$ and $\Sigma m_j$ where subscript j refers to the individual inorganic mineral component or kerogen (such as Quartz, Illite, Smectite, Kaolinite, Chlorite, ..., Kerogen).

In block 1121, optionally a data processor (such as the data collector/analyzer 313 of FIG. 4 or the CPU 144 of FIG. 1) is configured and operated to subtract a contribution of the inorganic mineral components from the IR spectrum of 1117 based on the mass fractions of the inorganic mineral components of the rock sample of 1119. For example, if the rock sample contains a mass fraction of Quartz equal to 5% of the sample(s), the IR spectrum of a pure Quart multiplied by 0.05 can be removed from the measured IR spectrum. Similar operations can be repeated for one or more other inorganic mineral components in the rock sample.

In block 1123, a data processor (such as the data collector/analyzer 313 of FIG. 4 or the CPU 144 of FIG. 1) is configured and operated to obtain a residuum IR spectrum representative of kerogen in the rock sample by subtracting a contribution of organic soluble components (including oil and bitumen) from the IR spectrum of 1117 or 1121 based on the mass fractions of the organic soluble components (including oil and bitumen) in the rock sample of 1113.

FIGS. 13A-13D illustrate exemplary measured DRIFT spectra in the region of the IR spectrum between 2600 and 3200 cm$^{-1}$ wherein are expressed prominent IR absorption bands associated with C—H vibrational modes in organic matter. The absorption bands in the native formation sample (FIG. 13A) in this region of the IR spectrum are a composite of all organic matter components in the sample, here comprising bitumen (in porosity) and kerogen (in matrix). From the soluble organic (non-kerogen) component mass fractions solved from the NMR measurement in 1113, the IR spectrum corresponding to the mass fraction of one or more soluble organic (non-kerogen) components is subtracted from the measured IR spectrum to leave a 'residuum' IR spectrum (FIG. 13C) containing IR absorption bands associated with C—H vibrational modes only in kerogen. For example, if the rock sample contains a mass fraction of bitumen equal to 10% of the sample(s), the IR spectrum of a pure bitumen multiplied by 0.1 can be removed from the measured IR spectrum. Similar operations can be repeated for other organic (non-kerogen) components in the rock sample, such as oil, identified by the NMR measurement. The residuum IR spectrum (FIG. 13C) is then representative of a pure kerogen (FIG. 13D) such that the kerogen-associated IR absorption bands in the residuum spectrum can be used to estimate properties of the kerogen in the rock sample.

In block 1125, a data processor (such as the data collector/analyzer 313 of FIG. 4 or the CPU 144 of FIG. 1) is configured and operated to analyze the residuum IR spectrum of 1123 to generate data that characterizes properties of kerogen in the rock sample, such as kerogen thermal maturity or kerogen density. In embodiments, such analysis can be performed for the region of the residuum IR spectrum between 2800 and 3100 cm$^{-1}$. Methods for the determination of kerogen properties from an IR spectrum are well-known to those skilled in the art and described in co-owned U.S. Pat. No. 8,906,690, U.S. Patent Publication No. 2017/0248011 and U.S. Patent Publication No. 2018/0188161, herein incorporated by reference in their entireties.

In block 1127, a data processor (such as the data collector/analyzer 313 of FIG. 4 or the CPU 144 of FIG. 1) is configured and operated to determine data representing matrix density of the rock sample. The determination of matrix density can be derived from the sum of the mass fractions of the inorganic mineral components and kerogen in the rock sample as determined from the spectroscopy measurement (block 1119) divided by their respective densities as given in Eqn. (4) above. The kerogen density that is used to determine matrix density can be determined from the analysis of the residuum IR spectrum as provided in block 1125.

In block 1129, a data processor (such as the data collector/analyzer 313 of FIG. 4 or the CPU 144 of FIG. 1) is configured and operated to determine data representing bulk volume of the rock sample. The determination of bulk volume ($V_{bulk}$) of the rock sample can be computed from the pore volume data of 1111 and the matrix density data of 1127 as follows:

$$V_{bulk} = \left(\frac{(m_s - (V_{pore} * \rho_{fluid}))}{\rho_{ma}}\right) + V_{pore}, \quad \text{Eqn. (10)}$$

where $m_s$ is the mass (in grams) of the rock sample as measured in 1105, $V_{pore}$ is the pore volume of the rock sample measured by NMR in 1111, $\rho_{fluid}$ is the fluid density of the fluid that saturates the rock sample, and $\rho_{ma}$ is the matrix density of the rock sample measured by spectroscopy in 1127.

The liquid density $\rho_{fluid}$ can be based on liquid densities obtained from density measurements completed on separate fluid samples (associated with the same rock sample) using established techniques or based on model estimates for the liquid densities using composition and established density models from petroleum thermodynamics. For example, the fluid that saturates the rock sample can contain multiple components (or compounds) and the liquid density $\rho_{fluid}$ of such fluid may be calculated using a number of well-established methods by one skilled in the art, including mixing rules (e.g., Eqn. (6) above), density correlations, corresponding states, and equation of state (with or without volume translation).

In block 1131, a data processor (such as the data collector/analyzer 313 of FIG. 4 or the CPU 144 of FIG. 1) is configured and operated to determine data representing porosity of the rock sample. The determination of porosity (φ) of the rock sample can be calculated from the pore volume data of 1111 and the bulk volume data of 1129 as follows:

$$\varphi = V_{pore}/V_{bulk}, \quad \text{Eqn. (11)}$$

where $V_{pore}$ is the pore volume of the rock sample measured by NMR in 1111, $V_{bulk}$ is the bulk volume of the rock sample as determined in 1129.

Rock Sample Porosity by Multi-Nuclear NMR Measurement

Embodiments of the present disclosure also include a workflow for measurement of porosity and saturations of cuttings (or some other rock sample with irregular shaped and/or sized pieces) using a multi-nuclear NMR workflow. Multiple techniques are described and claimed. One embodiment is based on the use of a fluid containing non-hydrogen nuclei (e.g., a fluorine-based fluid) in the multi-nuclear NMR workflow to determine the porosity of the cuttings (or some other rock sample with irregular shaped and/or sized pieces).

Note that NMR is routinely used as a fast and non-destructive method to analyze rock cores to provide information on pore volume, pore fluid saturations, and pore fluid typing in the lab. Generally, the NMR measurements are carried out at a Larmor frequency of 2 MHz for measuring $^1$H nuclei, which is similar to the frequency of NMR logging tools to allow for core-log integration. Furthermore, the rock core that is interrogated by the NMR measurements are uniformly cut cylindrical core plugs about 1.5"×1.5". The regular shape of the core plug gives a reliable bulk volume, measured by caliper, and is used along with the pore volume to obtain porosity. The size of the core plug results in a high filling factor in the NMR probe, thus a high signal-to-noise ratio (SNR). When cuttings are used in place of a cylindrical core plug, the small and irregularly shaped cuttings result in a low SNR for the NMR measurements and makes measurements of bulk volume more challenging.

In embodiments, the NMR measurements of the cuttings (or some other rock sample with irregular shaped and/or sized pieces) can be carried out at a frequency higher than 2 MHz (for example, at a frequency of 12 MHz) to address the challenge of low SNR from the cuttings (or some other rock sample with irregular shaped and/or sized pieces). The benefit of the higher-frequency measurement is to allow shorter echo spacings, which accommodates short T2 relaxation times that are characteristic of unconventional samples, and to improve the separation of fluids, namely free water, clay associated water, oil, bitumen, and kerogen.

Improvement in SNR can be achieved by going to a higher magnetic field as the SNR is proportional to $B_0^{1\sim7/4}$, where $B_0$ is the nominal field strength of the magnet, depending on the noise source (Mitchell, J., Gladden, L. F., Chandrasekera, M. L., Fordham, E. J., (2014) Low-field permanent magnets for industrial process and quality control Prog. Nucl. Magn. Reson. Spectros. 76, 1-60, Hoult, D. I., Richards, R. E., (1976) The signal-to-noise ratio of the nuclear magnetic resonance experiment J. Magn. Reson. 24, 71-85). However, in NMR analysis of conventional formations, pore-scale magnetic field distortions (so-called "internal gradients") caused by the solid/fluid susceptibility contrast can bring about complications; molecular diffusion through these internal gradients introduces an enhanced signal decay, leading to uncertainty in $T_2$ measurements (J. Mitchell, T. C. Chandrasekera, M. L. Johns, L. F. Gladden, E. J. Fordham (2010) Nuclear magnetic resonance relaxation and diffusion in the presence of internal gradients: the effect of field strength Phys. Rev. E 81, 026101). Since the internal gradients increase with the field strength, low field strength of 0.05 T (corresponding to a resonance frequency of 2 MHz for $^1$H) is considered the industry standard to provide quantitative measurements as well as for well-log calibration. On the other hand, the nanometer-scale pores in shale samples ensure that the spins explore the pore multiple times during a measurement and hence the gradient effects across a pore average out (M. D. Hürlimann, K. G. Helmer, T. M. de Swiet, P. N. Sen, and C. H. Sotak (1995) Spin echoes in a constant gradient and in the presence of simple restriction J. Magn. Reson. Ser. A 113, 260). Under these conditions, an increase in $B_0$ from 0.05 T to 1 T and possibly beyond results in only a slight increase in the rate of signal decay due to diffusion in the internal gradients, whilst attaining much better SNR (J. Mitchell, E. J. Fordham (2014) Contributed Review: Nuclear magnetic resonance core analysis at 0.3 T Rev. Sci. Instrum. 85, 111502).

The irregular shapes and sizes of the pieces of the rock sample makes measurement of bulk volume very difficult. Additionally, the irregular shapes and sizes of the pieces of the rock sample can have a lower filling factor in the RF probes resulting in lower signal to noise ratios. In embodiments, a methodology for measuring bulk volume of an irregularly sized and/or shaped rock sample (such as cuttings) is provided using $^{19}$F NMR measurements. Other solvents that could be used include ones with NMR active nuclei such as heavy water ($D_2O$), or solvents with other NMR active nuclei such as $^{13}$C and $^{31}$P. In combination with $^1$H NMR for the pore volume measurement, this provides a quick porosity measurement for unconventional shale samples. Additionally, the method can utilize a higher frequency NMR system in comparison to traditional core analysis workflows thereby addressing the SNR challenge. While the use of a higher frequency would make these experiments better, it is not a strict requirement for this workflow. The use of a higher field also allows for shorter echo spacing, which is beneficial for detecting short $T_2$ components found in unconventional samples. Additionally, the $T_1$ dependence with frequency of different components in shale (the clay associated water and viscous hydrocarbons), enable their better separation. An accurate porosity measurement combined with the ability for identifying different organic components makes this workflow a valuable analysis tool for unconventional reservoirs. The capability of measuring irregular-shaped samples with minimal instrumentation and supervision also opens up automated cutting analysis at either the laboratory environment (as part of cutting screening methodology,) or the wellsite.

Embodiments included herein may make use of $^{19}$F NMR measurements to find bulk volume with the integration with a $^1$H NMR measurement to obtain porosity. The method can employ a dual-tuned probe or other configuration that provides consistent sensitivity to volume for the $^{19}$F and $^1$H NMR measurements. Fluorine resonates at a Larmor frequency 5.9% less than that of $^1$H, which is within the tuning range of most probes. And, because we are observing subtle changes in volume, system stability and calibration can have a significant impact on the outcome. Higher field NMR systems yield better SNR, which is beneficial to measuring samples with low filling factor. And such systems also generally enable measurements at shorter echo spacings, which are useful for shale rock fluid typing and samples of low porosity.

Figure 14A:
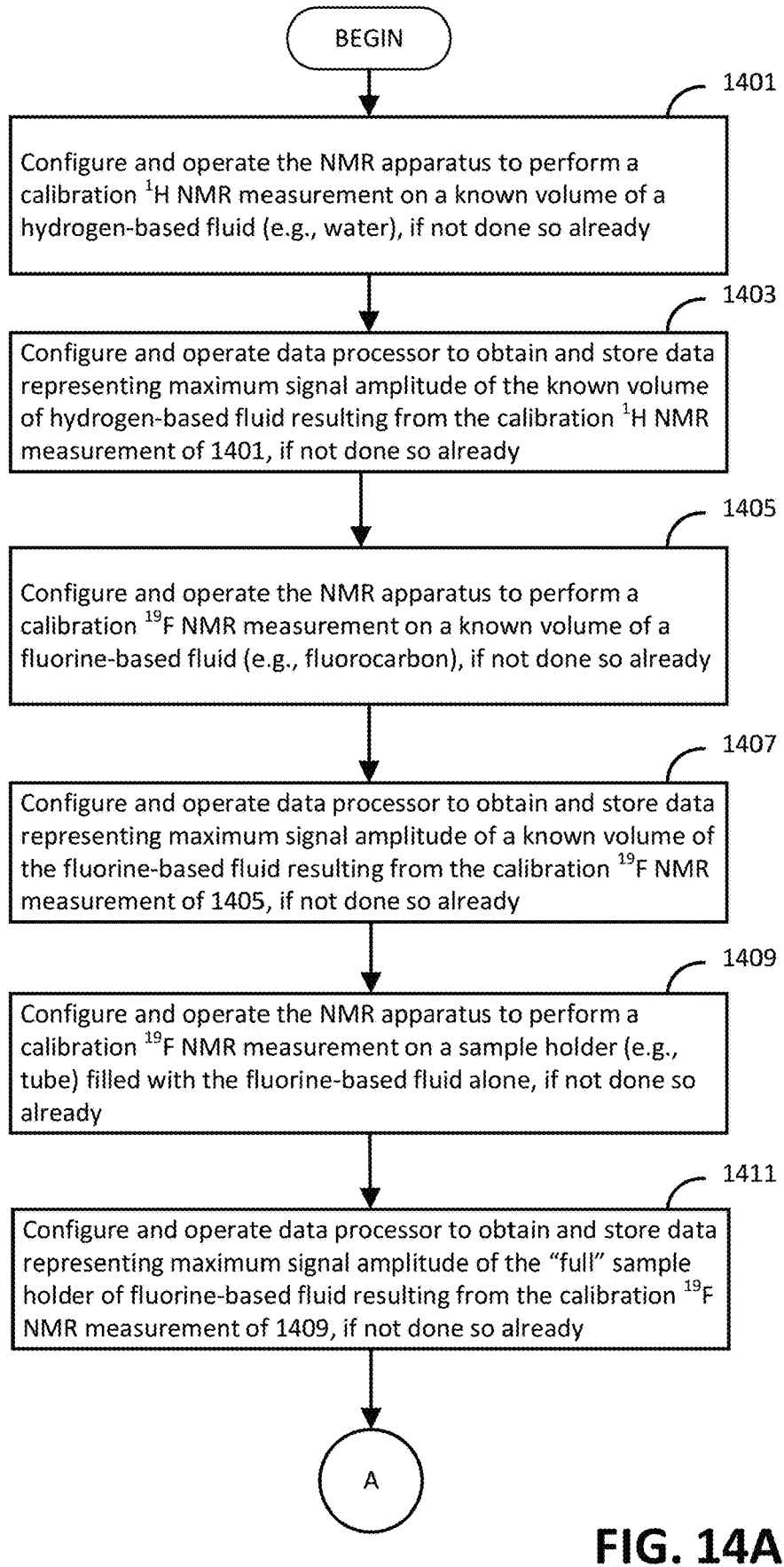
FIGS. 14A-14C, collectively, is a flowchart that illustrates an exemplary workflow that employs multi-nucleic NMR measurements on cuttings (or some other rock sample of irregularly shaped and/or sized pieces) to determine porosity of the rock sample.
Figure 14B:
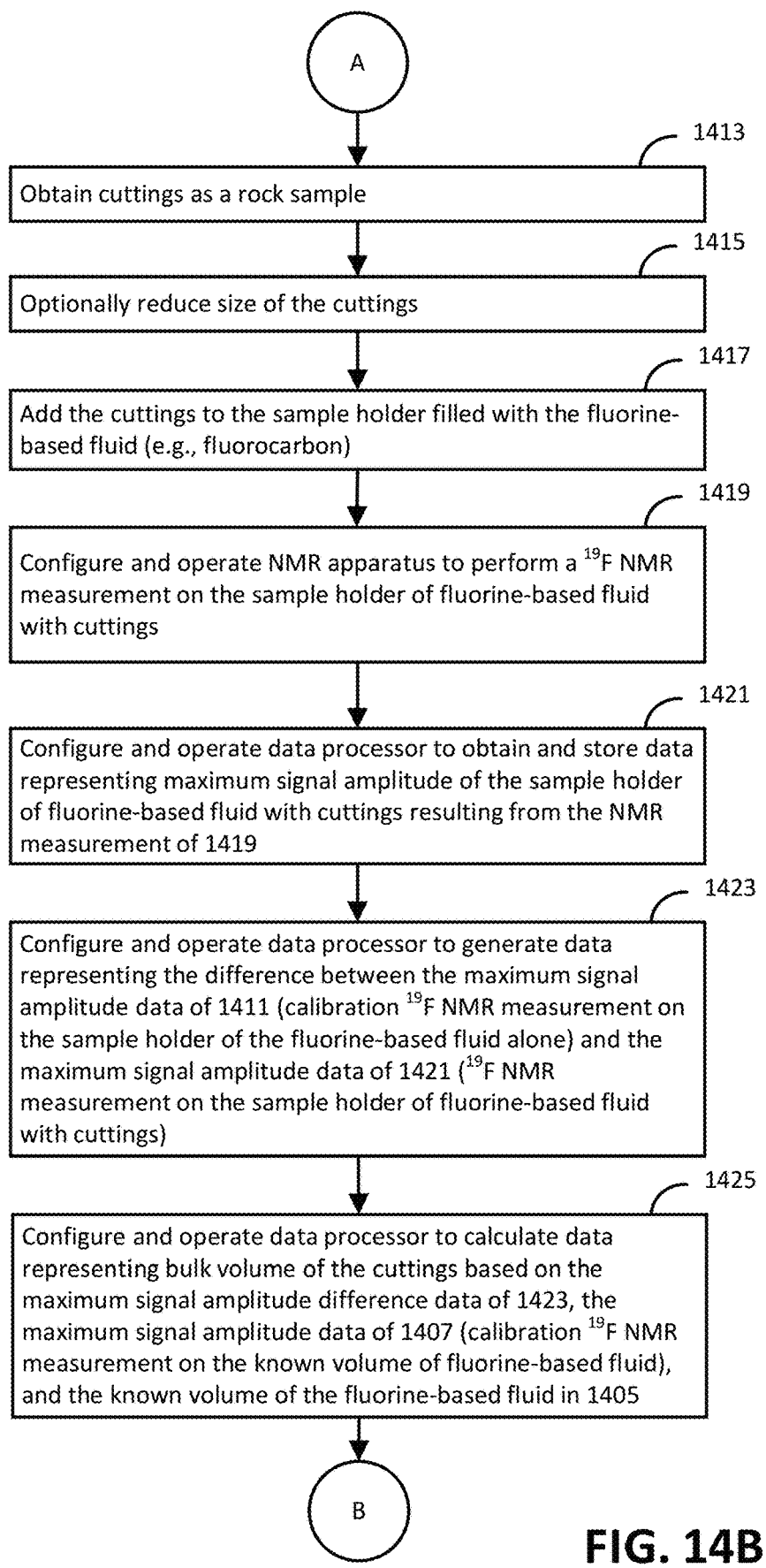
Figure 14C:
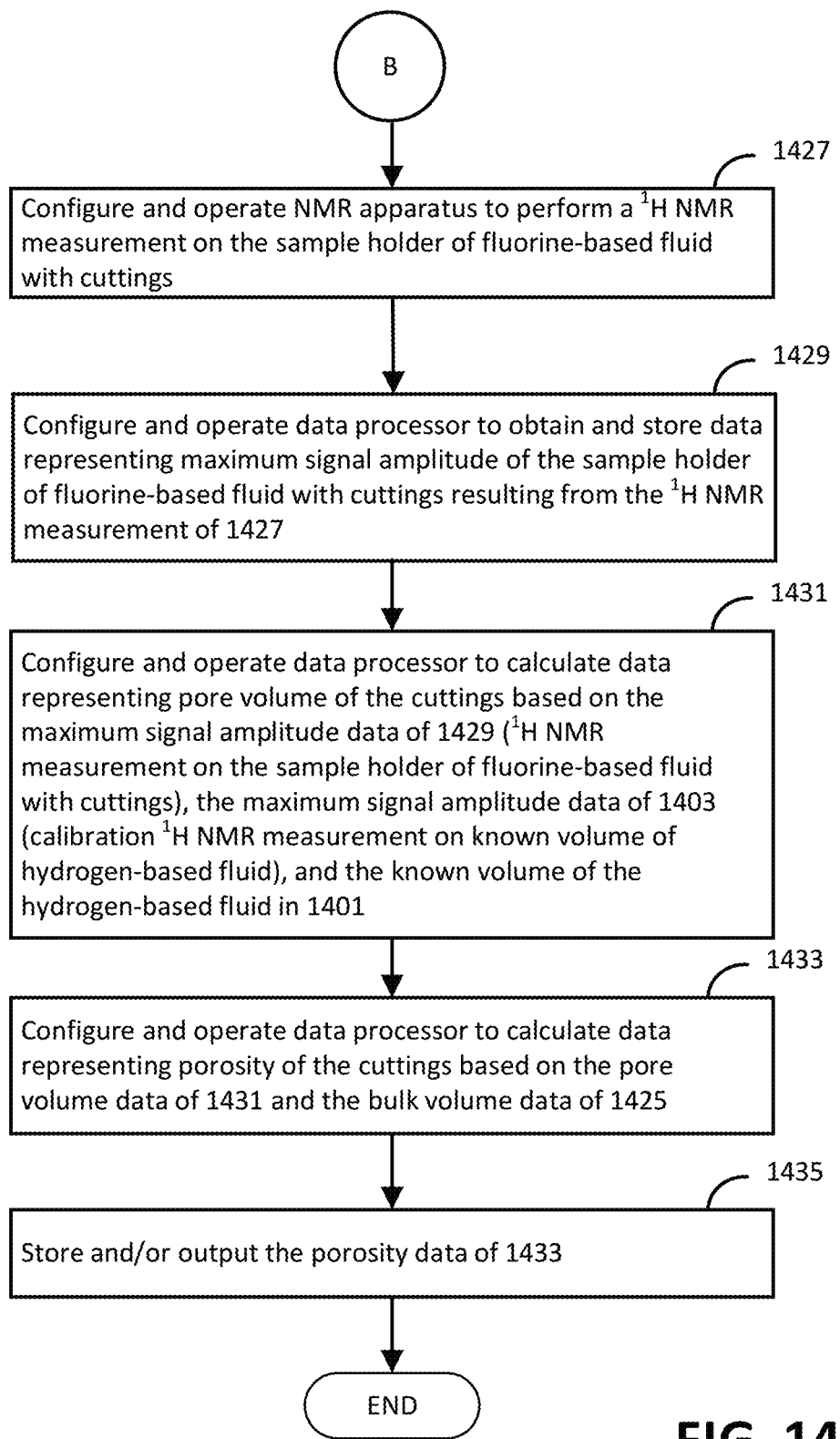

Calibrations for both the $^{19}$F and $^1$H NMR measurements can be made by multiple methods. One embodiment involves measuring the maximum signal amplitude of two known fluid volumes; water with an NMR measurement at an operating frequency for measuring hydrogen nuclei (which is referred to as a $^1$H NMR measurement), and a fluorine-based fluid (e.g., fluorocarbon) with an NMR measurement at an operating frequency for measuring fluorine nuclei (which is referred to as an $^{19}$F NMR measurement). An additional calibration $^{19}$F NMR measurement can be made on a sample holder that is "full" of the fluorine-based fluid, where just enough fluid is added to fill the entire measurable volume (or region) of the coil of the NMR apparatus. A rock sample can then be added to the same full tube of the fluorine-based fluid and the maximum signal amplitude acquired again. The difference in maximum signal amplitude between the fluorine-based fluid only and the fluorine-based fluid plus rock sample is the contribution from the bulk volume occupied by the rock sample. In embodiments, the time-varying signal amplitude of the respective NMR measurements can be derived by mono-exponential fitting of the magnetization decay that is measured by the NMR apparatus for the respective NMR measurements, and the maximum signal amplitudes of the respective NMR measurements can be determined from the maximum of the mono-exponential fit of the magnetization decay for the respective NMR measurements. An embodiment of this methodology is described below with reference to the flowchart of FIGS. 14A-14C.

In block 1401, an NMR apparatus (such as NMR apparatus 140 of FIG. 2) is configured and operated to perform a calibration $^1$H NMR measurement on a known volume of a hydrogen-based fluid (e.g., water), if not done so already. The calibration $^1$H NMR measurement of 1401 is performed at an operating frequency for measuring hydrogen nuclei. The tube labeled A in FIG. 15A depicts a known volume of fluid, such as the hydrogen-based fluid (e.g., water), used in 1401.

In block 1403, a data processor (such as the data collector/analyzer 225 of FIG. 2) is configured and operated to obtain and store data representing maximum signal amplitude of the known volume of hydrogen-based fluid which results from the calibration $^1$H NMR measurement of 1401, if not done so already. In embodiments, the time-varying signal amplitude of the calibration $^1$H NMR measurement of 1401 can be derived by mono-exponential fitting of the magnetization decay that is measured by the NMR apparatus in 1401, and the maximum signal amplitude of the calibration $^1$H NMR measurement of 1401 can be determined from the maximum of the mono-exponential fit of the magnetization decay that is measured by the NMR apparatus in 1401.

In block 1405, the NMR apparatus (such as NMR apparatus 140 of FIG. 2) is configured and operated to perform a calibration $^{19}$F NMR measurement on a known volume of a fluorine-based fluid (e.g., a fluorocarbon such as $C_{10}F_{22}N$), if not done so already. The calibration $^{19}$F NMR measurement of 1405 is performed at an operating frequency for measuring fluorine nuclei. The tube labeled B in FIG. 15A depicts a known volume of fluid, such as the fluorine-based fluid (e.g., fluorocarbon) used in 1405.

In block 1407, a data processor (such as the data collector/analyzer 225 of FIG. 2) is configured and operated to obtain and store data representing maximum signal amplitude of the known volume of the fluorine-based fluid which results from the $^{19}$F NMR measurement of 1405, if not done so already. In embodiments, the time-varying signal amplitude of the calibration $^{19}$F NMR measurement of 1405 can be derived by mono-exponential fitting of the magnetization decay that is measured by the NMR apparatus in 1405, and the maximum signal amplitude of the calibration $^{19}$F NMR measurement of 1405 can be determined from the maximum of the mono-exponential fit of the magnetization decay that is measured by the NMR apparatus in 1405.

In block 1409, the NMR apparatus (such as NMR apparatus 140 of FIG. 2) is configured and operated to perform a calibration $^{19}$F NMR measurement on a sample holder (e.g., tube) filled with the fluorine-based fluid, if not done so already. In this case, the sample holder can be filled with just enough fluorine-based fluid to fill the entire measurable volume (or region) of the coil of the NMR apparatus. The calibration $^{19}$F NMR measurement of 1407 is performed at an operating frequency for measuring fluorine nuclei. The tube labeled C in FIG. 15A depicts a sample holder (e.g., tube) filled with fluorine-based fluid used in 1409.

In block 1411, a data processor (such as the data collector/analyzer 225 of FIG. 2) is configured and operated to obtain and store data representing maximum signal amplitude of the "full" sample holder of fluorine-based fluid which results from the $^{19}$F NMR measurement of 1409, if not done so already. In embodiments, the time-varying signal amplitude of the calibration $^{19}$F NMR measurement of 1409 can be derived by mono-exponential fitting of the magnetization decay that is measured by the NMR apparatus in 1409, and the maximum signal amplitude of the calibration $^{19}$F NMR measurement of 1409 can be determined from the maximum of the mono-exponential fit of the magnetization decay that is measured by the NMR apparatus in 1409.

In block 1413, cuttings (or some other irregularly sized and/or shaped rock sample) are collected or otherwise obtained from a formation and used as a rock sample.

In block 1415, optionally, the cuttings (or some other irregularly sized and/or shaped rock sample) can be reduced in size to a size suitable for the multi-nucleic NMR measurements (1419 and 1427).

In block 1417, the cuttings (or other irregularly sized and shaped rock sample) are added to the sample holder that is filled with the fluorine-based fluid (e.g., fluorocarbon), which was tested in 1409.

In block 1419, the NMR apparatus (such as NMR apparatus 140 of FIG. 2) is configured and operated to perform an 19F NMR measurement on the sample holder of fluorine-based fluid with the cuttings (or other rock sample), which is tube D in FIG. 15A. The $^{19}$F NMR measurement of 1419 is performed at an operating frequency for measuring fluorine nuclei. Note that the tube labeled D in FIG. 15A depicts a sample holder (e.g., tube) of fluorine-based fluid and cuttings labeled E as used in 1419.

In block 1421, a data processor (such as the data collector/analyzer 225 of FIG. 2) is configured and operated to obtain and store data representing maximum signal amplitude of the sample holder of fluorine-based fluid with cuttings (or other rock sample) which results from the $^{19}$F NMR measurement of 1419. In embodiments, the time-varying signal amplitude of the $^{19}$F NMR measurement of 1419 can be derived by mono-exponential fitting of the magnetization decay that is measured by the NMR apparatus in 1419, and the maximum signal amplitude of the $^{19}$F NMR measurement of 1419 can be determined from the maximum of the mono-exponential fit of the magnetization decay that is measured by the NMR apparatus in 1419.

In block 1423, a data processor (such as the data collector/analyzer 225 of FIG. 2) is configured and operated to generate data representing the difference between the maximum signal amplitude data of 1411 (for the calibration $^{19}$F NMR measurement on the sample holder full of the fluorine-based fluid alone, which is tube C in FIG. 15A) and the maximum signal amplitude data of 1421 (for the $^{19}$F NMR measurement on the sample holder of fluorine-based fluid with cuttings or other rock sample, which is tube D in FIG. 15A).

In block 1425, a data processor (such as the data collector/analyzer 225 of FIG. 2) is configured and operated to calculate data representing bulk volume of the cuttings or other rock sample based on the maximum signal amplitude difference data of 1423, the maximum signal amplitude data of 1407 (for the calibration $^{19}$F NMR measurement on the known volume of fluorine-based fluid, which is tube B in FIG. 15A), and the known volume of the fluorine-based fluid in 1405. The maximum signal amplitudes from the multi-nucleic NMR measurements can be notated with the labels for the tubes used in FIG. 15A such that $S_C$ and $S_D$ are the maximum signal amplitudes of tubes C and D, which is the maximum signal of the sample space determined in 1411 and 1421, respectively. In this case, the data representing bulk volume ($V_{bulk}$) of the cuttings or other rock sample can be given as:

$$V_{bulk}=(V_B*(S_C-S_D))/S_B, \qquad \text{Eqn. (12)}$$

where $V_B$ is the known volume of the fluorine-based fluid in 1405, $S_B$ is the maximum signal amplitude of the known-volume of fluorine-based fluid in 1407, $S_C$ is the maximum signal amplitude of the full tube C of the fluorine-based fluid in 1411, and $S_D$ is the maximum signal amplitude of the tube D of fluorine-based fluid and cuttings in 1421.

In block 1427, the NMR apparatus (such as NMR apparatus 140 of FIG. 2) is configured and operated to perform a $^1$H NMR measurement on the sample holder of fluorine-based fluid with the cuttings (or other rock sample), which is tube D in FIG. 15A. The $^1$H NMR measurement of 1427 is performed at an operating frequency for measuring hydrogen nuclei. The blocks labeled E immersed in tube D in FIG. 15A depict cuttings (or other rock sample) used in 1427.

In block 1429, a data processor (such as the data collector/analyzer 225 of FIG. 2) is configured and operated to obtain and store data representing maximum signal amplitude of the $^1$H NMR measurement of 1427. In embodiments, the time-varying signal amplitude of the $^1$H NMR measurement of 1427 can be derived by mono-exponential fitting of the magnetization decay that is measured by the NMR apparatus in 1427, and the maximum signal amplitude of the $^1$H NMR measurement of 1427 can be determined from the maximum of the mono-exponential fit of the magnetization decay that is measured by the NMR apparatus in 1427.

In block 1431, a data processor (such as the data collector/analyzer 225 of FIG. 2) is configured and operated to calculate data representing pore volume of the cuttings or other rock sample based on the maximum signal amplitude of 1429 (for the $^1$H NMR measurement on the sample holder of fluorine-based fluid with cuttings or other rock sample, which is tube D in FIG. 15A), the maximum signal amplitude data of 1403 (for the calibration $^1$H NMR measurement on the known volume of hydrogen-based fluid, which is tube A in FIG. 15A), and the known volume of the hydrogen-based fluid in 1401. In this case, the data representing pore volume ($V_{pore}$) of the cuttings or other rock sample can be given as:

$$V_{pore}=(V_A*S_E)/S_A, \qquad \text{Eqn. (13)}$$

where $V_A$ is the known volume of the hydrogen-based fluid in 1401, $S_E$ is the maximum signal amplitude of the $^1$H NMR measurement on the sample holder of fluorine-based fluid with the cuttings (or other rock sample) of 1427, and $S_A$ is the maximum signal amplitude of the known-volume of hydrogen-based fluid in 1403.

In block 1433, a data processor (such as the data collector/analyzer 225 of FIG. 2) is configured and operated to calculate data representing porosity of the cuttings or other rock sample based on the pore volume data of 1431 and the bulk volume data of 1425. Specifically, the porosity ($\varphi$) of the cuttings or other rock sample can be calculated from Eqn. (7) by dividing the pore volume data of 1431 by the bulk volume data of 1425.

In block 1435, a data processor (such as the data collector/analyzer 225 of FIG. 2) can be configured and operated to store and/or output the porosity data of 1433.

Figure 15B:
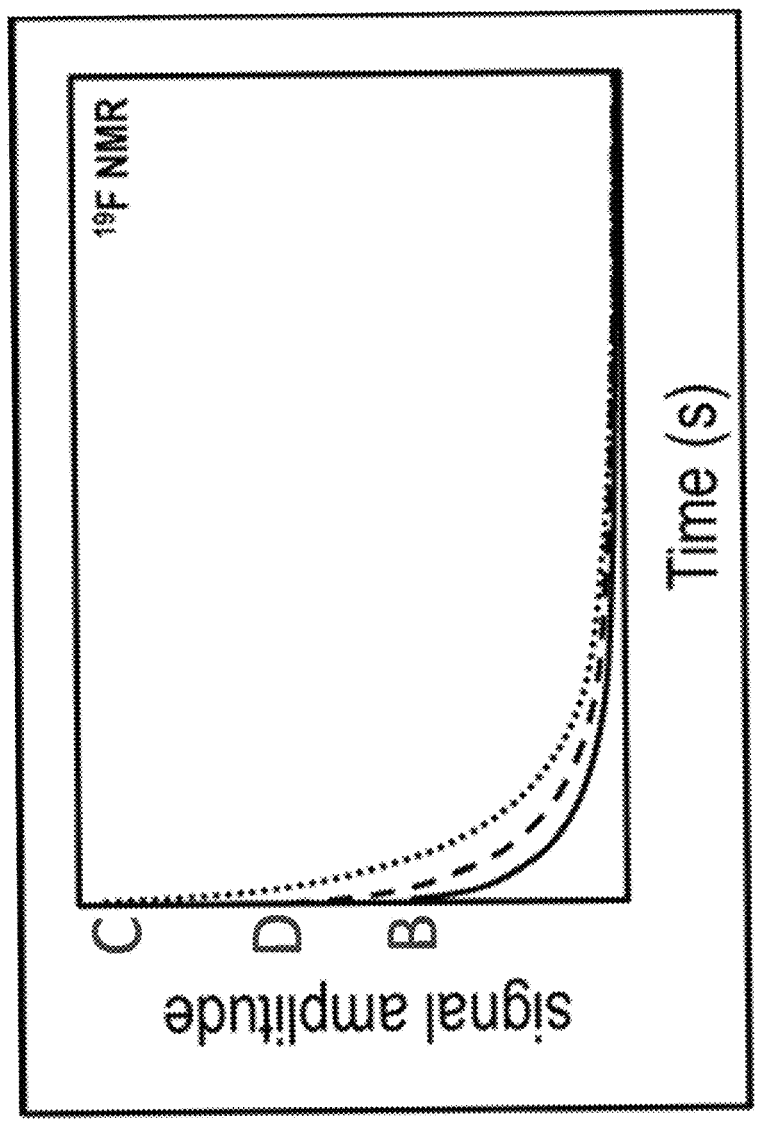
FIG. 15B is a plot of exemplary NMR signals acquired by the NMR measurements of the workflow. The NMR signal labeled B is the result of the calibration $^{19}F$ NMR measurement performed on the sample B of FIG. 15A, which is the known-volume of the fluorine-based fluid (fluorocarbon). The NMR signal labeled C is the result of the calibration $^{19}F$ NMR measurement performed on the sample C of FIG. 15A, which is the sample holder filled with the fluorine-based fluid (fluorocarbon). The NMR signal labeled D is the result of the $^{19}F$ NMR measurement performed on the sample D of FIG. 15A, which is the sample holder filled with the fluorine-based fluid (fluorocarbon) and cuttings.
Figure 15A:
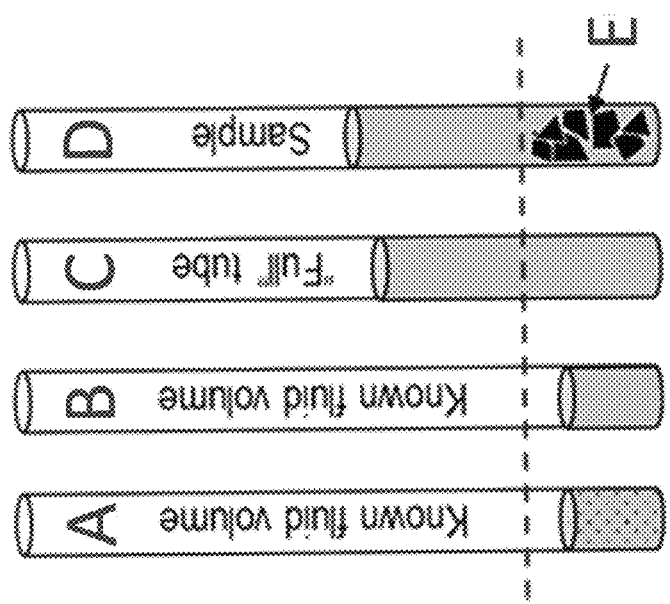
FIG. 15A is a schematic diagram of the samples that are subject to the multi-nucleic NMR measurements in the workflow of FIGS. 14A-14C. The sample labeled A depicts a known-volume of a fluid containing hydrogen-nuclei (e.g., water). The sample labeled B depicts a known-volume of a fluid containing non-hydrogen nuclei, particularly a fluorine-based fluid (e.g., fluorocarbon). Both the sample A and the sample B are subject to separate calibration NMR measurements in the workflow of FIGS. 14A-14C. The sample labeled C depicts a sample holder (tube) filled with the fluorine-based fluid (e.g., fluorocarbon) that is subject to a calibration NMR measurement in the workflow of FIGS. 14A-14C. The sample labeled D depicts a sample holder (tube) filled with the fluorine-based fluid (e.g., fluorocarbon) together with the sample labeled E that depicts cuttings (or some other rock sample of irregularly shaped and/or sized pieces) that is subject to an NMR measurement in the workflow of FIGS. 14A-14C. The probe volume (or coil volume) of the NMR apparatus that performs the NMR measurements of the workflow of FIGS. 14A-14C is depicted as a horizontal dashed line.

FIG. 15B is a plot of exemplary NMR signals acquired by the NMR measurements of the workflow. The NMR signal labeled B is the result of the calibration $^{19}$F NMR measurement performed on the known-volume of a fluorine-based fluid (fluorocarbon) and acquired in 1405. The NMR signal labeled C is the result of the calibration $^{19}$F NMR measurement performed on the sample holder filled with the fluorine-based fluid (fluorocarbon) and acquired in 1409. The NMR signal labeled D is the result of the $^{19}$F NMR measurement performed on the sample holder filled with the fluorine-based fluid (fluorocarbon) and cuttings and acquired in 1419.

Figure 15C:
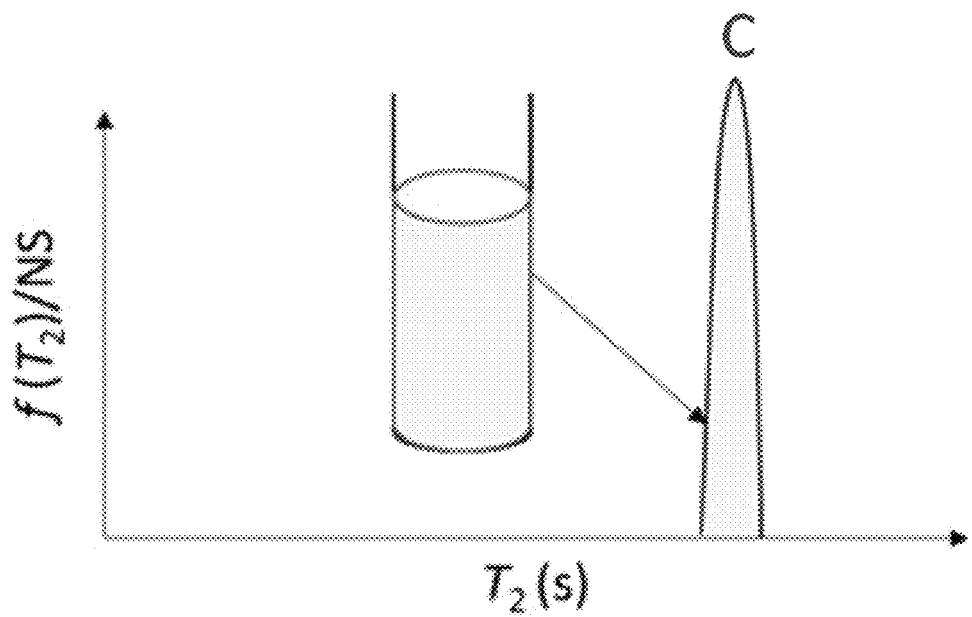
FIG. 15C is a schematic illustration of the volume (labeled C) measured by the calibration $^{19}F$ NMR measurement performed on the sample C of FIG. 15A, which is the sample tube filled with the fluorine-based fluid alone.
Figure 15D:
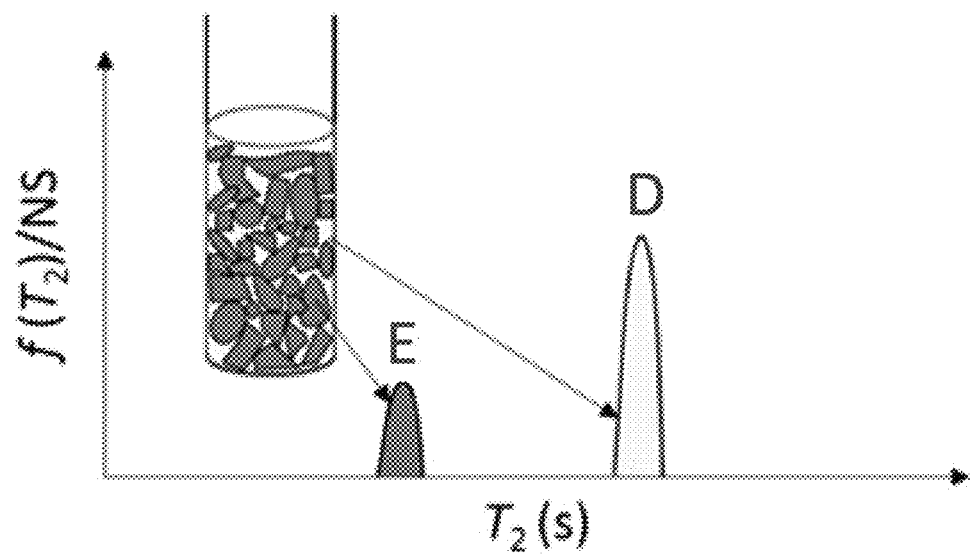
FIG. 15D is a schematic diagram of the volume (labeled D) measured by the $^{19}F$ NMR measurement performed on the sample D of FIG. 15A (which is the sample holder with the fluorine-based fluid and cuttings) together with the volume (labeled E) measured by a $^{1}H$ NMR measurement performed on the sample D of FIG. 15A. Note that the difference between the volume C of FIG. 15C and the volume D of FIG. 15D corresponds to bulk volume of the cuttings, while the volume E of FIG. 15D corresponds to the pore volume of the cuttings.

FIG. 15C is a schematic illustration of the volume (labeled C) measured by the calibration $^{19}$F NMR measurement of 1409 performed on the sample holder filled with the fluorine-based fluid alone. FIG. 15D is a schematic illustration of the volume (labeled D) measured by the $^{19}$F NMR measurement of 1419 performed on the sample holder with the fluorine-based fluid and cuttings together with the volume (labeled E) measured by the $^1$H NMR measurement of 1427 performed on the sample holder with the fluorine-based fluid and cuttings. Note that the difference between the volume C of FIG. 15C and the volume D of FIG. 15D corresponds to bulk volume of the cuttings as determined in 1425, while the volume E of FIG. 15D corresponds to the pore volume of the cuttings as determined in 1431.

From the bulk volume measured with the $^{19}$F NMR measurements and the pore volume measured with the $^1$H NMR measurement, the porosity of the irregularly sized and/or shaped rock sample can be determined in 1433 independent of grain density or mass. The sequence of measurements has the flexibility to be done in any order. For example, when the probe is tuned to the correct frequency, the decay of fluorine nuclei will not interfere with decay of hydrogen protons and vice versa so that the rock sample can be included in the sample holder filled with the fluorine-base and be measured by the $^1$H NMR measurement to detect the decay of hydrogen nuclei alone without difficulty.

Note that the analysis of drill cuttings is a progressive step toward understanding the reservoir and implementing NMR porosity with multi-nuclear measurements at the wellsite which can provide valuable information. Methods in the disclosure deliver accurate porosity of drill-cuttings and have applications both at the wellsite and in the laboratory. In addition, this new approach to porosity measurements opens the door to further core analysis on hard to obtain or unconsolidated rock samples.

Applications

The porosity and other properties of the cuttings or other rock samples as determined by the workflow(s) described herein relate to RQ and/or CQ of a reservoir.

In some embodiments, porosity and other properties of rock samples determined by the workflow(s) described herein can be used as inputs to determine the design of a well completion as well as the operation of downhole equipment and surface equipment that produce hydrocarbons from the reservoir. For example, parts of an unconventional reservoir with relatively low RQ and/or relatively low CQ due to poor porosity and/or poor permeability and other parameters can possibly be bypassed or isolated by stages of a completion, while other parts of the unconventional reservoir with relatively high RQ and/or relatively high CQ due to sufficient porosity and/or sufficient permeability and other parameters can be accessed by stages of the completion that provide for fracturing (and/or other stimulation or treatment) and production of hydrocarbons and possibly other reservoir fluids from the reservoir.

In some embodiments, porosity and other properties of rock samples determined by the workflow(s) described herein can be used as inputs to a reservoir simulator to determine an optimal design of a completion as well as the operation of downhole equipment and surface equipment that produce hydrocarbons from the reservoir.

In other embodiments, geomechanical properties of a formation may be needed for a variety of reasons without the use of a logging while drilling tool or wireline tool. There may be a need to complement tool failure.

In other embodiments, the porosity and other properties of the rock samples determined by the workflow(s) described herein can be used to drill the wellbore without core data or log information. A drilling regime may include multiple lateral wells from one initial wellbore and the costs for core and/or log data may be unreasonably burdensome. Some embodiments may use a drill string with no tools for logging. Some embodiments may be performed on site in near real time without time for data actualization, that is, the drill string may remain in the wellbore as people timely use the information available to them without remote mathematical analysis and without operating time lag. Some embodiments may manipulate the data in time to guide the completion time. Also, some of the techniques to address these issues, such as laboratory measurements and some logs, require post-analysis, and interpretation of the data that cannot be done within the drilling timeframe.

Further, while some vertical pilot wells are logged and evaluated in an unconventional play, stimulated horizontal wells are rarely logged or cored. The cost of acquiring the information and/or the associated rig time needed during acquisition (which means that the rig cannot be used for drilling or stimulation elsewhere) are two main reasons for this trend. The solution must be low cost and efficient in terms of delivery times (i.e., in real-time or near real-time). It must not introduce any inefficiency into the development program (such as extended rig time for data acquisition) and must be based on a simple workflow that can be carried out at the wellsite by non-experts.

Also, the hydraulic fracturing stimulation of unconventional organic shale reservoirs is performed today in mostly horizontal wells where heterogeneities of petrophysical and mechanical properties along the well are known to be very significant. Staging requires the identification of sections of the well with both good reservoir quality and good completion quality. Completion quality estimates rely on changes in elastic, rock strength, and stress properties along the well reflect variations (heterogeneity) of mechanical properties along the well.

The embodiments as described herein relate to methods for recovering hydrocarbons from a formation including collecting a formation sample, forming the sample into particles, exposing the sample to a cleaning fluid, and analyzing the sample. Embodiments also relate to methods for recovering hydrocarbons from a formation including the steps of collecting a formation sample, first exposing the sample to a cleaning fluid, forming the sample into particles, exposing the sample to a second cleaning fluid and analyzing the sample.

Time and location are important considerations for embodiments of this procedure. The analyzing occurs in less than an hour and/or in less than 24 hours in some embodiments. The analyzing occurs before recovering hydrocarbons begins in some embodiments or after producing hydrocarbons begins in some embodiments. The analyzing may occur during reservoir characterization during production. Some embodiments may use equipment within 500 meters of a wellbore. In some embodiments, analyzing occurs while drilling the formation.

Figure 16:
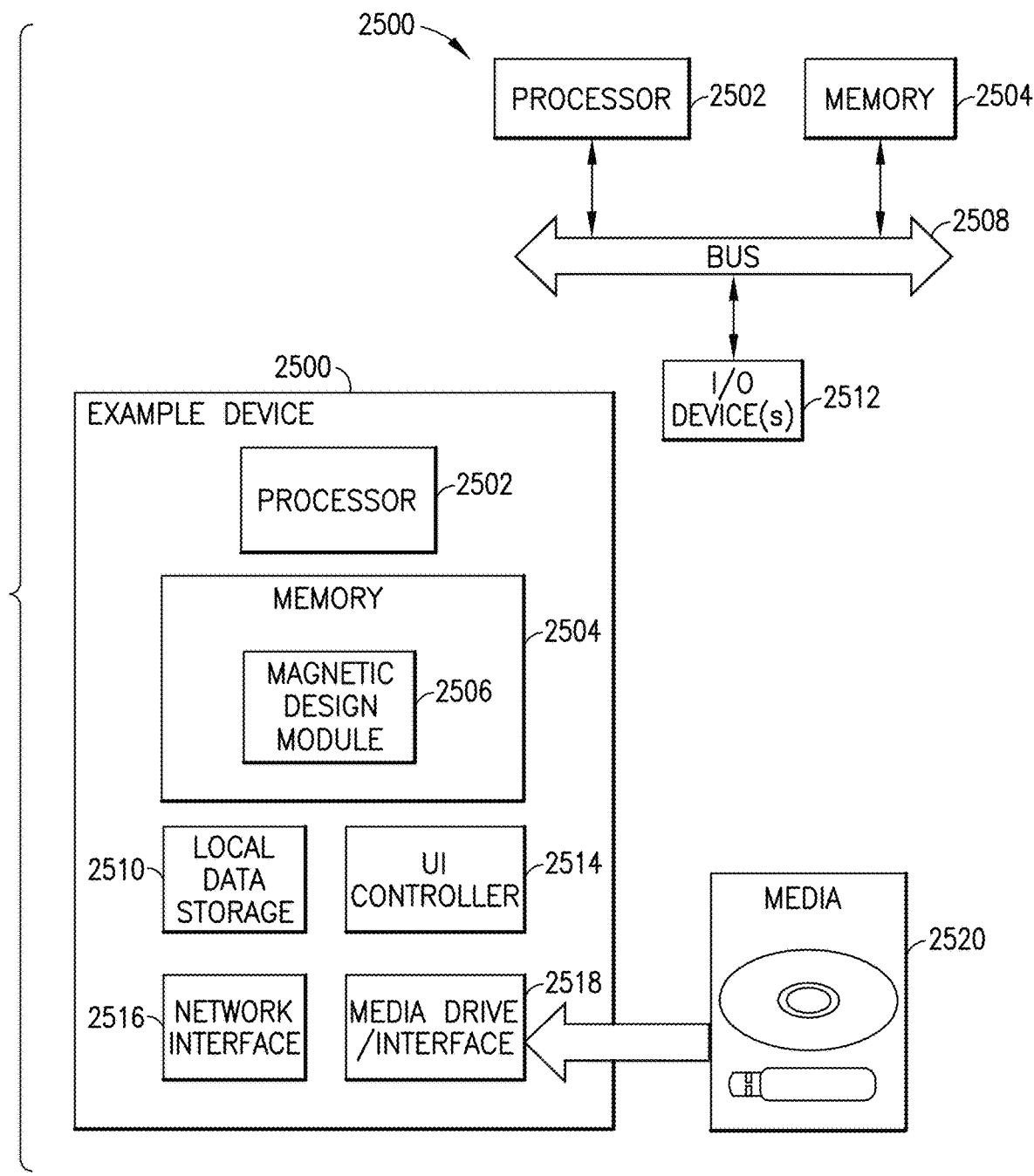
FIG. 16 illustrates an example computing device, with a processor and memory, that can be configured to implement various embodiments of methods and system as discussed in this disclosure.

FIG. 16 illustrates an example device 2500, with a processor 2502 and memory 2504 that can be configured to implement various embodiments of methods and system as discussed in this disclosure. Memory 2504 can also host one or more databases and can include one or more forms of volatile data storage media such as random-access memory (RAM), and/or one or more forms of nonvolatile storage media (such as read-only memory (ROM), flash memory, and so forth).

Device 2500 is one example of a computing device or programmable device and is not intended to suggest any limitation as to scope of use or functionality of device 2500 and/or its possible architectures. For example, device 2500 can comprise one or more computing devices, programmable logic controllers (PLCs), etc.

Further, device 2500 should not be interpreted as having any dependency relating to one or a combination of components illustrated in device 2500. For example, device 2500 may include one or more computers such as a laptop computer, a desktop computer, a mainframe computer, etc., or any combination or accumulation thereof.

Device 2500 can also include a bus 2508 configured to allow various components and devices, such as processors 2502, memory 2504, and local data storage 2510, among other components, to communicate with each other.

Bus 2508 can include one or more of any of several types of bus structures, including a memory bus or memory controller, a peripheral bus, an accelerated graphics port, and a processor or local bus using any of a variety of bus architectures. Bus 2508 can also include wired and/or wireless buses.

Local data storage 2510 can include fixed media (e.g., RAM, ROM, a fixed hard drive, etc.) as well as removable media (e.g., a flash memory drive, a removable hard drive, optical disks, magnetic disks, and so forth).

One or more input/output (I/O) device(s) 2512 may also communicate via a user interface (UI) controller 2514, which may connect with I/O device(s) 2512 either directly or through bus 2508.

In one possible implementation, a network interface 2516 may communicate outside of device 2500 via a connected network.

A media drive/interface 2518 can accept removable tangible media 2520, such as flash drives, optical disks, removable hard drives, software products, etc. In one possible implementation, logic, computing instructions, and/or software programs comprising elements of module 2506 may reside on removable media 2520 readable by media drive/interface 2518.

In one possible embodiment, input/output device(s) 2512 can allow a user to enter commands and information to device 2500 and also allow information to be presented to the user and/or other components or devices. Examples of input device(s) 2512 include, for example, sensors, a keyboard, a cursor control device (e.g., a mouse), a microphone, a scanner, and any other input devices known in the art. Examples of output devices include a display device (e.g., a monitor or projector), speakers, a printer, a network card, and so on.

Various processes of present disclosure may be described herein in the general context of software or program modules, or the techniques and modules may be implemented in pure computing hardware. Software generally includes routines, programs, objects, components, data structures, and so forth that perform particular tasks or implement particular abstract data types. An implementation of these modules and techniques may be stored on or transmitted across some form of tangible computer-readable media. Computer-readable media can be any available data storage medium or media that is tangible and can be accessed by a computing device. Computer readable media may thus comprise computer storage media. "Computer storage media" designates tangible media, and includes volatile and non-volatile, removable and non-removable tangible media implemented for storage of information such as computer readable instructions, data structures, program modules, or other data. Computer storage media include, but are not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other tangible medium which can be used to store the desired information, and which can be accessed by a computer.

The flowchart and block diagrams in the figures illustrate the architecture, functionality, and operation of possible implementations of systems and methods and according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of means or step plus function elements in the claims below are intended to include any structure, material, or act for performing the function in combination with other claimed elements as specifically claimed. The description of the present disclosure has been presented for purposes of illustration and description but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

Although a few example embodiments have been described in detail above, those skilled in the art will readily appreciate that many modifications are possible in the example embodiments without materially departing from the scope of the present disclosure, described herein. Accordingly, such modifications are intended to be included within the scope of this disclosure as defined in the following claims. In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. It is the express intention of the applicant not to invoke 35 U.S.C. § 112, paragraph 6 for any limitations of any of the claims herein, except for those in which the claim expressly uses the words 'means for' together with an associated function.

Having thus described the disclosure of the present application in detail and by reference to embodiments thereof, it will be apparent that modifications and variations are possible without departing from the scope of the disclosure defined in the appended claims.

The invention claimed is:

1. A method for characterizing properties of a rock sample obtained from a subterranean formation, comprising:
    performing an NMR measurement on the rock sample;
    determining data characterizing matrix density of the rock sample, wherein the rock sample comprises cuttings and wherein the cuttings comprise cleaned cuttings; and
    using results of the NMR measurements and the data characterizing matrix density of the rock sample to determine data representing at least one property of the rock sample.

2. The method according to claim 1, further comprising:
    analyzing the results of the NMR measurement to determine data characterizing pore volume of the rock sample;
    calculating data representing bulk volume of the rock sample based on the pore volume data and the matrix density data of the rock sample; and
    calculating data representing porosity of the rock sample based on the pore volume data of the rock sample and the bulk volume data of the rock sample, wherein the data representing porosity of the rock sample is part of the data representing at least one property of the rock sample.

3. The method according to claim 1, wherein:
    the data characterizing matrix density of the rock sample is determined from results of a matrix density measurement.

4. The method according to claim 2, wherein:
    the matrix density measurement involves at least one of the following methods: IR spectroscopy, a pycnometer method, X-ray diffraction, pyrolysis, or rock eval method.

* * * * *